(12) United States Patent
Maunder et al.

(10) Patent No.: US 11,771,587 B1
(45) Date of Patent: Oct. 3, 2023

(54) PORTABLE RECHARGEABLE THERAPY PODS

(71) Applicant: Snapbac, LLC, Franklin, TN (US)

(72) Inventors: Jamieson Maunder, San Diego, CA (US); Kevin M. Bello, Franklin, TN (US)

(73) Assignee: Snapbac, LLC, Franklin, TN (US)

( * ) Notice: Subject to any disclaimer, the term of this patent is extended or adjusted under 35 U.S.C. 154(b) by 0 days.

(21) Appl. No.: 17/517,861

(22) Filed: Nov. 3, 2021

Related U.S. Application Data

(60) Provisional application No. 63/238,590, filed on Aug. 30, 2021.

(51) Int. Cl.
| | | |
|---|---|---|
| *A61F 7/00* | (2006.01) | |
| *A61F 7/02* | (2006.01) | |
| *H05B 3/34* | (2006.01) | |

(52) U.S. Cl.
CPC ............... *A61F 7/007* (2013.01); *H05B 3/34* (2013.01); *A61F 2007/0075* (2013.01); *A61F 2007/0078* (2013.01); *A61F 2007/0094* (2013.01); *A61F 2007/0233* (2013.01)

(58) Field of Classification Search
CPC .............. A61F 7/007; A61F 2007/0071; A61F 2007/0073; A61F 2007/0075; A61F 2007/0078; A61F 2007/0086; A61F 2007/0087; A61F 2007/0088; A61F 2007/0093; A61F 2007/0094; A61F 2007/0095; A61F 2007/0096; A61F 2007/0225; A61F 2007/0228; A61F 2007/0233; H05B 3/34
See application file for complete search history.

(56) References Cited

U.S. PATENT DOCUMENTS

| | | | |
|---|---|---|---|
| 4,741,338 A | * | 5/1988 | Miyamae .................. A61F 7/00 607/112 |
| 4,846,176 A | | 7/1989 | Golden |
| 5,682,748 A | | 11/1997 | DeVilbiss et al. |
| 5,800,490 A | | 9/1998 | Patz et al. |
| 5,970,718 A | | 10/1999 | Arnold |
| 7,739,748 B2 | | 6/2010 | Nilforushan et al. |
| 8,397,518 B1 | | 3/2013 | Vistakula |
| 8,876,875 B1 | | 11/2014 | Nilforushan et al. |
| 8,907,251 B2 | | 12/2014 | Larsen et al. |

(Continued)

FOREIGN PATENT DOCUMENTS

JP      200825052 A    2/2008

OTHER PUBLICATIONS

Translation of JP2008025052A, Date: Feb. 7, 2008.

*Primary Examiner* — Kaitlyn E Smith
*Assistant Examiner* — Bradford C. Blaise
(74) *Attorney, Agent, or Firm* — Nicholas Pfeifer; Smith & Hopen, P. A.

(57) ABSTRACT

A thermal therapy pod adapted to maintain a desired therapeutic temperature and change temperature on the fly without needing to be heated or chilled by an external thermal source. The therapy pod is self-contained and uses an electric powered thermal transferring element that can provide both heat and cold therapy. The temperature and duration of use may be controlled using an application on a mobile device. The therapy pod can be positioned on a user using straps, wraps, sleeves, or other wearable therapy pod retaining devices.

19 Claims, 19 Drawing Sheets

(56) References Cited

U.S. PATENT DOCUMENTS

| | | | |
|---|---|---|---|
| 9,029,736 B2 | 5/2015 | Lavin, Jr. | |
| 10,406,024 B2 | 10/2019 | Evans et al. | |
| 2005/0193742 A1* | 9/2005 | Arnold | A62B 17/005 62/3.5 |
| 2008/0046047 A1 | 2/2008 | Jacobs | |
| 2013/0102944 A1* | 4/2013 | DiGrazia | A61F 13/0273 602/43 |
| 2015/0101788 A1 | 4/2015 | Smith et al. | |
| 2015/0216718 A1* | 8/2015 | Diller | A61F 7/007 607/96 |
| 2016/0000600 A1* | 1/2016 | Lee | A61F 7/00 607/109 |
| 2016/0074210 A1* | 3/2016 | Chen | A61F 7/007 607/96 |
| 2016/0158510 A1* | 6/2016 | Casasanta, III | A61F 7/007 604/290 |
| 2018/0042761 A1* | 2/2018 | Smith | A44C 5/0007 |
| 2018/0071138 A1* | 3/2018 | Armstrong | A61F 7/007 |
| 2018/0110266 A1* | 4/2018 | Lee | H01L 27/16 |
| 2018/0153735 A1* | 6/2018 | Shim | A61F 7/007 |
| 2019/0350752 A1* | 11/2019 | Aguiar | A61F 7/02 |
| 2020/0206023 A1* | 7/2020 | Pathak | A61F 7/0085 |
| 2021/0030141 A1* | 2/2021 | Goo | A61B 90/98 |
| 2021/0052418 A1* | 2/2021 | Breiter | A61F 7/007 |

\* cited by examiner

PORTABLE RECHARGEABLE THERAPY PODS

CROSS-REFERENCE TO RELATED APPLICATIONS

This nonprovisional application claims priority to provisional application No. 63/238,590, entitled "PORTABLE RECHARGEABLE THERAPY PODS," filed Aug. 30, 2021 by the same inventor(s).

BACKGROUND OF THE INVENTION

1. Field of the Invention

This invention relates, generally, to thermal therapy equipment. More specifically, it relates to portable, electrically rechargeable thermal therapy pods.

2. Brief Description of the Prior Art

The art of heating and cooling the human body for prevention and/or treatment of injuries is well known and frequently practiced. Thermal therapy treatments provide many benefits including pain relief, increased flexibility, and alteration of a body's core temperature to improve on a person's ability to function properly. The state of the art has progressed greatly from manually holding bags of ice and warm towels to specialized wrapping devices containing hot/cold packs. These hot/cold packs are generically referred herein as thermal transferring elements (TFE's).

There currently exist numerous methods for applying and securing TFE's. One such method is manually holding a TFE, which has clear downsides, such as the difficulty in holding the TFE in hard-to-reach locations and restricting the use of at least one hand. Another method is attaching a TFE to a body part using straps, wraps, adhesives, or other means. However, the conventional methods are often limited in where the TFEs can be secured with respect to a person's body. The ability to securely position TFEs is often a limitation on the useability of these devices.

Other major limitations in the current state of TFE's include the limited duration during which the TFE can maintain its desired therapeutic temperature, the need to reheat or refreeze the TFE, and the inability to modify the therapeutic temperature of the TFE on the fly.

Accordingly, what is needed is a thermal therapy pod adapted to be secured at any location on a user's body and adapted to maintain a desired therapeutic temperature and change temperature on the fly without needing to be heated or chilled by an external thermal source. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved thermal therapy pod is now met by a new, useful, and nonobvious invention.

The novel structure includes a thermal therapy pod. In some embodiments, the thermal therapy pod has an elongated, thin main body with a thickness residing between an inner surface and an outer surface. The thermal therapy pod includes one or more electric powered thermal transferring elements residing between the inner surface and the outer surface. The thermal therapy pod includes a fan configured to dissipate heat created from operating the electric powered thermal transferring element to an ambient environment. Some embodiments further include a thermally conductive layer between the application surface of the electric powered thermal transferring element and the inner surface of the main body, wherein the thermally conductive layer is comprised of thermally conductive material.

Some embodiments further include a removable cover configured to temporarily interconnect with the main body. In some embodiments the interconnection occurs via a plurality of magnets disposed within the cover or the main body. In some embodiments, the thermal therapy pod further includes the interconnection between the cover and the main body being sufficiently sized to accommodate a retaining fabric between the cover and the main body when the cover and main body are interconnected.

In some embodiments the cover and the main body are flexible and resilient. As a result, the thermal therapy pod can flex about contours of a user's body.

In some embodiments, the cover houses a battery and a power transferring element configured to transfer electrical power from the cover to the main body for operating the electric powered thermal transferring element and the fan. In some embodiments, a wireless power transmitter is disposed in the cover and a wireless power receiver is disposed in the main body. The transmitter and receiver are respectively positioned at a predetermined position, such that the power transmitter can transfer power to the power receiver when the cover is interconnected with the main body.

Some embodiments of the thermal therapy pod include one or more charging pins on the cover and one or more charging pin receipts on the main body to transfer electrical power between the cover and the main body. Each of the charging pin receipts are positioned to receive the charging pins when the cover is interconnected with the main body. In some embodiments, the main body has the charging pins, and the cover has the charging pin receipts. Some embodiments of the cover include a charging port or wireless power receiver disposed therein for recharging the battery.

In some embodiments, the thermal therapy pod further includes a current switching circuit. The current switching circuit is configured to control a direction of a current to the electric powered thermal transferring element. Moreover, the electric powered thermal transferring element has an application side facing towards the inner surface of the main body of the therapy pod and a dissipation side facing towards the outer surface of the body of the therapy pod. The application side produces heat when the current flows in a first direction and becomes cold when the current flows in a second direction, opposite direction.

Some embodiments of the thermal therapy pod include a wireless communication system configured to communicate with a mobile device. Some embodiments of the thermal therapy pod include a plurality of vent holes through which the fan can discharge heat. In some embodiments, the thermal therapy pod has a thermostat for precisely determining the temperature the thermal therapy pod.

In some embodiments, the thermal therapy pod has a plurality cooling channels. Each cooling channel is in fluidic communication with the fan via a proximal aperture. The cooling channels also include a distal aperture leading out of the main body. Thus, the fan can direct air through the cooling channels to discharge heat from the electric powered thermal transferring element.

In some embodiments, the distal apertures are oriented to draw in or discharge air away from the inner surface of the main body. In some embodiments, each cooling channel passes along the electric powered thermal transferring element. Some embodiments further include a heat sink residing in overlying relation to the electric powered thermal transferring element. In some embodiments, the cooling channels are in open fluidic communication with the heat sinks, such that air passes around the heat sink to further aid in heat dissipation.

In some embodiments, the thermal therapy pod further includes recesses in the main body configured to receive the cover and the cover having a thickness generally equal to or less than a depth of the recesses, such that the cover does not extend outwardly beyond the outer surface of the main body. In some embodiments, the thermal therapy pod further includes male and corresponding female components for aligning and interconnecting the cover with the main body.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
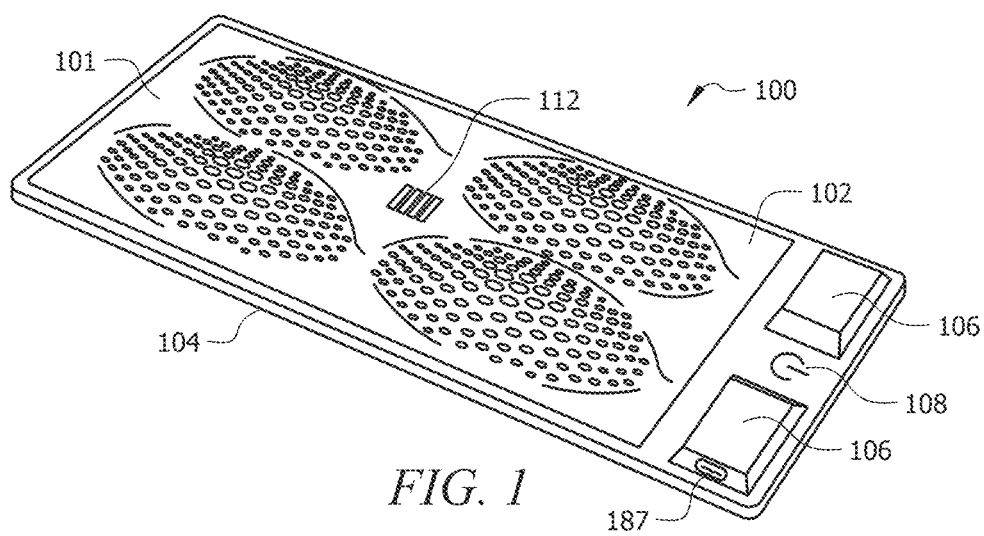
FIG. 1 is perspective view of an embodiment of the present invention.

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention. It is also to be understood that the various features described herein may be used with the various embodiments described herein.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a self-contained thermal therapy pod ("TTP") having an electric powered thermal transferring element ("ETFE"). The TTP can be positioned on a user using straps, wraps, sleeves, or other wearable therapy pod retaining devices including the multi-layer garment disclosed in U.S. Pat. No. 8,876,875 to Applicant. In some embodiments, the self-contained TTP is adapted to provide both heat and cold therapy and the self-contained aspect allows the TTP to be positioned at any location with the proper retainment device. Furthermore, in some embodiments, the TTP is independent of any retaining devices, thereby making the device more universally useable by consumers. In some embodiments, the TTP includes retention straps attached to or attachable to the main body.

Some embodiments are configured to be used with clothing items configured to secure the TTP up against a user's body with or without an intermediate portion of clothing residing between the user's body and the TTP. In some embodiments the TTP is secured in place against the user's body via clothing items having a degree of compression or tension that applies a force on the TTP in a direction generally towards the user's body. The layer of clothing configured to apply a force on the TTP is generally referred to herein as a retaining layer. In some embodiments, the retaining layer is at least partially comprised of a mesh-like fabric having a plurality of holes disposed therethrough. In some embodiments, the retaining layer is comprised of a heat resistant material to withstand the heat dissipated from the TTP, for example, the heat dissipated from a fan in the TTP. In some embodiments, the retaining layer is comprised of a heat resistant material to withstand 113 degrees Fahrenheit. In some embodiments, the retaining layer is comprised of a heat resistant material to withstand 110 degrees Fahrenheit.

Referring now to FIGS. 1-7, an embodiment of TTP 100 includes main body 101 having outer surface 102 and inner surface 104. Outer surface 102 is intended to face away from the user's body 105 and is intended to dissipate unnecessary heat away from TTP 100 and preferably user's body 105. Inner surface 104 is intended to face towards user's body 105 and provide thermal therapy to the user.

Figure 4:
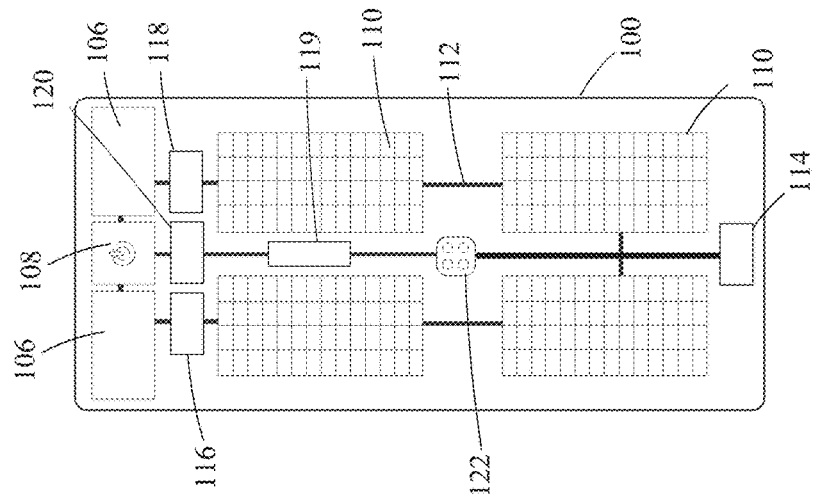
FIG. 4 is a cross-sectional view of an embodiment of the present invention.
Figure 3:
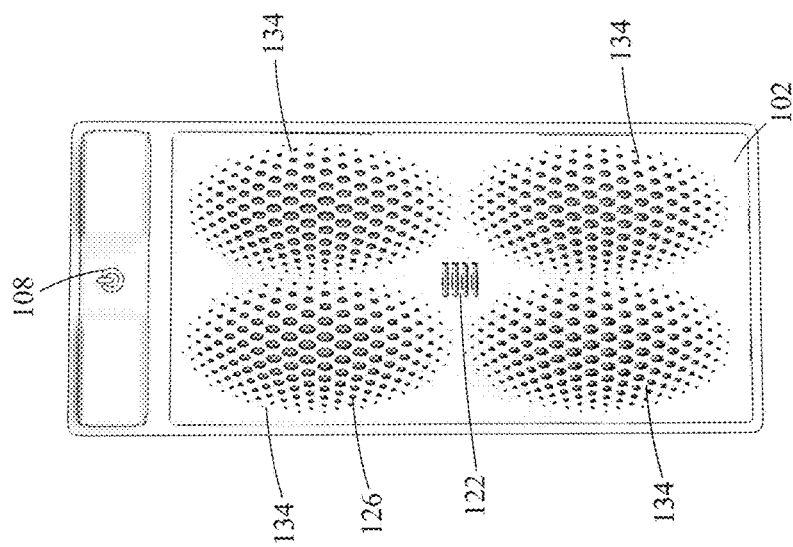
FIG. 3 is a top view of an embodiment of the present invention.

As best exemplified in FIG. 4, TTP 100 includes a plurality of components residing within main body 101. In some embodiments, TTP 100 includes one or more batteries 106, power actuator 108, one or more ETFEs 110, and the necessary wiring 112 to provide electrical power from batteries 106 to the various components. In some embodiments, TTP 100 further includes one or more of wireless communication circuitry 114, thermostat 116, temperature feedback circuitry 118, current switching circuitry 120, and indicator light 122, which may indicate the amount of power and/or whether TTP 100 is providing cold therapy or heat therapy. Some embodiments further include current and/or voltage regulator 119 to adjust the electrical power provided to ETFEs 110 to regulate the output temperature of ETFEs 110.

The various components may reside within a single component housing or may reside within one of several subdivided sections within main body 101. Subdivided sections can be insulated to better control the flow of heat within the therapy pod. Some embodiments, as will be explained in subsequent sections may include one or more of the various TTP components residing within a detachable cover.

In some embodiments, TTP 100 includes thermostat 116 and temperature feedback circuitry 118 to maintain the desired temperature of ETFEs 110 and in turn the temperature experienced by the user. Feedback circuitry 118 monitors the temperature of ETFEs 110 and/or the other components or sections of TTP 100, in a continuous or timed manner. By continuously monitoring the temperature, TTP 100 is able to ensure that ETFEs 110 do not exceed a certain safe threshold temperature and that ETFEs 110 maintain a desired temperature. Feedback circuitry 118 is in communication with power actuator 108 to selectively provide and cut power to ETFEs 110 as needed to control the temperature of TTP 100.

An embodiment further includes a safety switch that monitors heat within the component housing and is adapted to automatically shut down ETFEs 110 or reverse the current to switch which side of the Peltier ETFEs 110 are producing heat and cold. The safety switch may also automatically shut the system off after a predetermined duration of use.

In an embodiment, TTP 100 includes wireless communication system 114 including logic and circuitry capable of wirelessly communicating to a controller, e.g., a computer, mobile device 115, or other controller known to a person of ordinary skill in the art. Wireless communication system 114 may communicate via Bluetooth, NFC, WIFI, other wireless communication protocols known to a person of ordinary skill in the art. Controller 115 likewise uses a communication protocol that corresponds to the protocol used by TTP 100.

Figure 2:
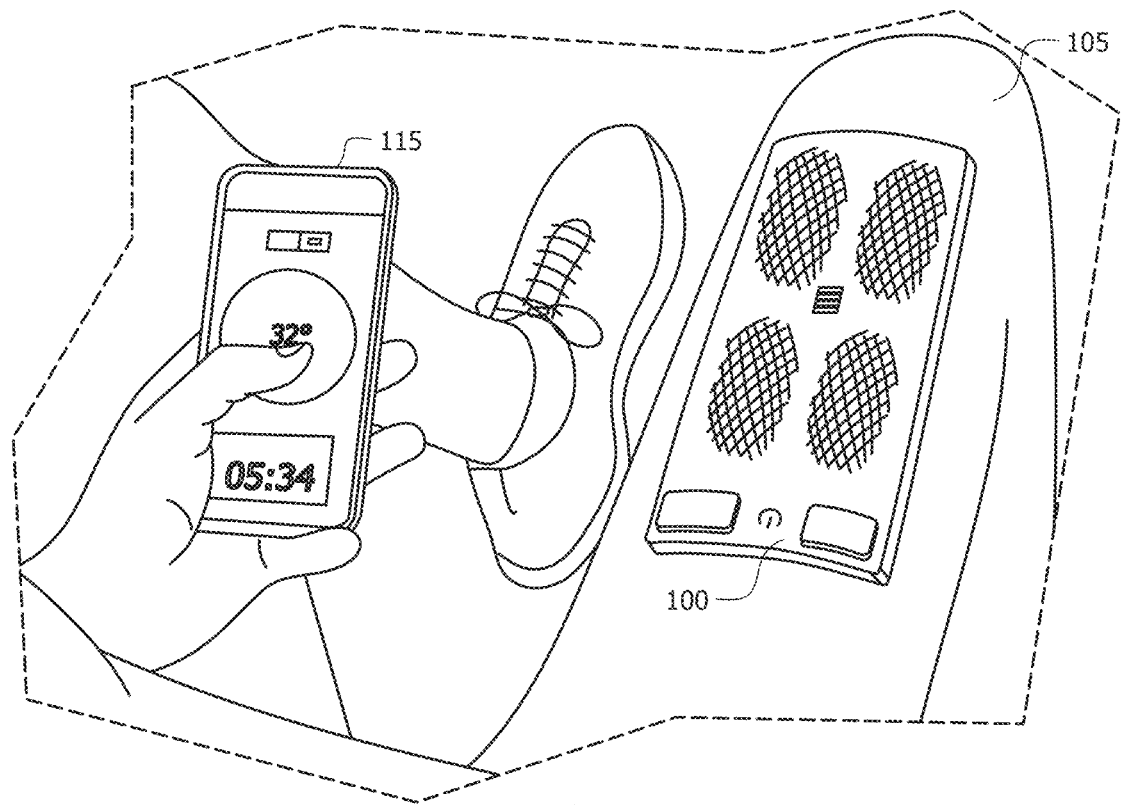
FIG. 2 is perspective view of an embodiment of the present invention controlled by an application on a mobile device.

Controller 115 provides a user with the ability to power TTP 100 on or off, control the exact temperature of TTP 100, and control/monitor the duration of use. As depicted in FIG. 2, a graphic user interface provides the user with the necessary information to operate and adjust the operation of TTP 100. The user is also provided with helpful information pertaining to operational metrics during use.

In an embodiment, controller 115 further includes preset selections for temperature and duration of use. Controller 115 can also provide presets based on the desired use of TTP 100. Non-exclusive presets include a "warm up" preset, a "cool down" preset, a "cold recovery" preset, a 'heat recovery" preset, and a "training" preset. Each preset is designed to adjust TTP 100 to a set temperature for a certain duration of time. An embodiment also includes the ability to create presets within the user application on controller 115. Controller 115 may also provide the option to automatically turn TTP 100 on and off based on time delays, time of day, or sensors on TTP 100 that detect body heat when TTP 100 is secured to a user.

An embodiment of TTP 100 further includes the ability to store and transfer usage data from TTP 100 to controller 115 or other computer device. The data can be transferred wirelessly from TTP 100 to the controller or can be downloaded through a wired connection 185 between the controller and data port 187 in TTP 100. Usage data can also be transmitted to a coach, trainer, or doctor for assessment.

Data port 187 can also operate as a charging port for recharging internal batteries 106 on TTP 100.

In an embodiment, batteries 106 are housed within the component housing and are charged through charging port 187. An embodiment may also include a housing access and replaceable batteries. TTP 100 may also include a separate battery compartment and said compartment may be accessible for battery replacement. An embodiment of TPP 100 may further include wireless charging in place or in addition to a charge port that charges the batteries through a wired connection. For example, the cover and the main body may have the necessary coils 190, 192, respectively, to allow for inductive charging between the two (see FIG. 20).

An embodiment of TTP 100 includes a mechanically actuatable power button or switch 108 to turn TTP 100 on and off. An embodiment further includes mechanically actuatable preset switches for operation without a mobile device or computer.

TTP 100 may include indicator light 122 disposed on outer surface 102, side walls 132 or cover 150 of TTP 100. Indicator light 122 may include a blue light to indicate that TTP 100 has initiated a cooling session and a red light to indicate that TTP 100 has initiated a heating session. Alternatively, or additionally, TTP 100 may have an indicator light that provides a visual indication of the power level and/or the on/off status of TTP 100.

In some embodiments, main body 101 is flexible and configured to conform to the surface shape of a user's body. In addition, main body 101 has relatively thin profile to enable the TTP to be easily retained against user's body 105 without being overly cumbersome. In some embodiments, TTP 100 has a total thickness less than 1 inch. In some embodiments, TTP 100 has a total thickness between 0.25 and 1 inch. In some embodiments, TTP 100 has a total thickness less than 1.5 inches.

In some embodiments, main body 101 includes a thermally conductive material to aid in the transfer of heat to or from the therapy pod. Some embodiments further include thermally conductive layer 124 adjacent to inner surface 104. Thermally conductive layer 124 is comprised of thermally conductive material. In such embodiments, thermally conductive layer 124 resides between inner surface 104 and ETFEs 110. The thermally conductive material may be comprised of any thermally conductive material known to a person of ordinary skill in the art, such as a soft silicone. In addition, thermally conductive layer 124 may comprise a chamber filled with a thermally conductive gel or fluid. ETFEs 110 are adjacent to or in direct contact with the thermally conductive material. The thermally conductive material or gel helps spread the heat or cold created by ETFEs 110 to a greater surface area on inner surface 104.

In some embodiments, ETFEs 110 are Peltier devices. A Peltier device is a temperature altering device that creates a heat flux between two materials when a voltage is applied across the two materials. One side of the Peltier device will increase in temperature while the other side decreases in temperature.

In embodiments employing Peltier ETFEs 110, voltage is applied across an application side to a dissipation side of the Peltier ETFEs 110. The application side is oriented towards inner surface 104 of TTP 100, while the dissipation side is oriented away from inner surface 104 of TTP 100. In some embodiments, Peltier ETFEs 110 are flexible in shape to allow the Peltier devices to flex with TTP 100.

As best shown in FIG. 4, an embodiment of TTP 100 includes four flexible Peltier ETFEs 110 in series connected to two batteries 106. TTP 100 includes power actuator 108 configured to close and open a switch that controls the flow of electrical current to power Peltier ETFEs 110. TTP 100 further includes current switching circuit 120 that can reverse the flow of current to Peltier ETFEs 110. The flow of current determines whether the application side of ETFEs 110 become hotter or colder with respect to the dissipation side of Peltier ETFE 110. When the current moves in a first direction, the application side will increase in heat while the dissipation side becomes colder. When current switching circuit 120 reverses the current to move in the opposite second direction, the temperature of the application side will decrease while the temperature of the dissipation side increases. By controlling current switching circuit 120, a user can switch TTP 100 from a cold therapy pod to a hot therapy pod.

Some embodiments include a sufficient number of Peltier ETFEs 110 to equate to roughly 90% or more of the surface area of inner surface 104. This coverage ensures adequate thermal therapy delivery to a desired location on a user's body. In some embodiments, TTP 100 includes Peltier ETFEs 110 spaced about roughly 50% or more of the surface area of inner surface 104. In some embodiments, TTP 100 includes Peltier ETFEs 110 spaced about roughly 60% or more of the surface area of inner surface 104. In some embodiments, TTP 100 includes Peltier ETFEs 110 spaced about roughly 70% or more of the surface area of inner surface 104. In some embodiments, TTP 100 includes Peltier ETFEs 110 spaced about roughly 80% or more of the surface area of inner surface 104.

Because Peltier ETFEs 110 create a relatively large amount of heat during operation, TTP 100 further includes one or more vents 126, heat sinks 128, and/or fans 130 to dissipate the operational heat away from Peltier ETFEs 110, thereby preventing the Peltier ETFEs 110 and other components in TTP 100 from overheating. As will be explained in subsequent paragraphs, some embodiments of TTP 100 include vents 126 disposed in outer surface 102 and/or in side walls 132 of TTP 100.

Figure 5:
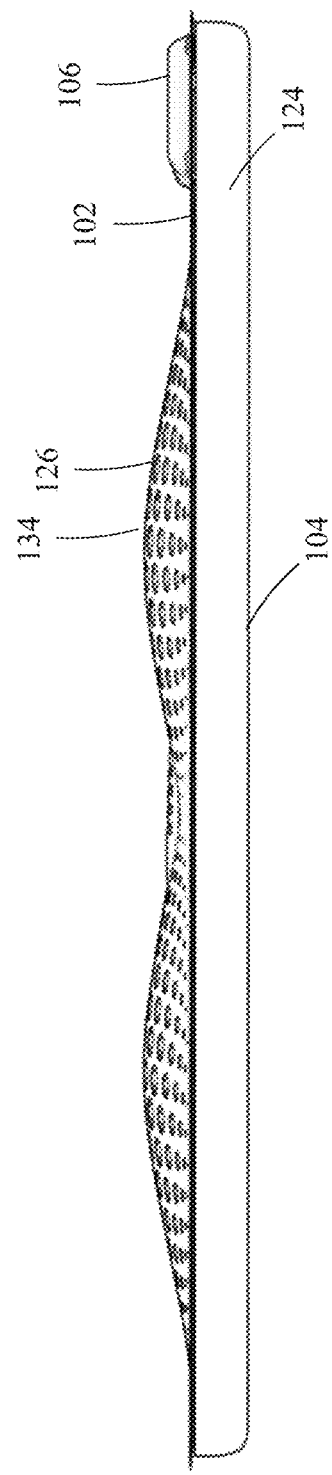
FIG. 5 is a side elevation view of an embodiment of the present invention.
Figure 7:
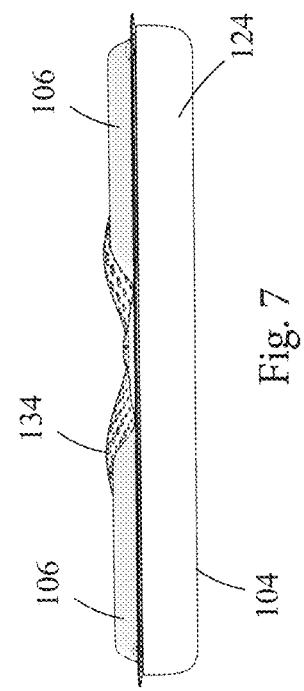
FIG. 7 is an end view of an embodiment of the present invention opposite of the view in FIG. 6.
Figure 6:
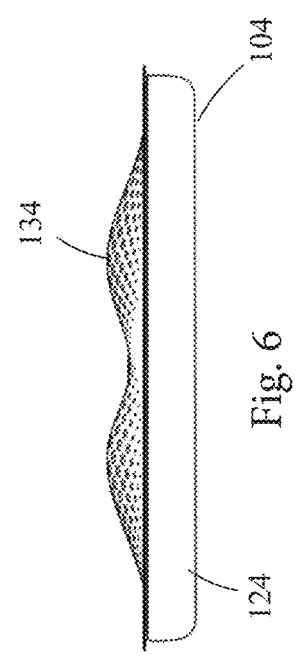
FIG. 6 is an end view of an embodiment of the present invention.

As shown best in FIG. 5, some embodiments of TTP 100 include dome structures 134 extending outwardly from outer surface 102. In some embodiments, dome structures 134 are disposed above each Peltier ETFE 110 to accommodate heat sinks and/or increase the surface area above each Peltier ETFE 110. Greater surface area results in more vent holes 126 and more vent holes 126 result in greater air flow to better dissipate operational heat from Peltier ETFE 110. In addition, domes 134 are used to reduce the thickness of the therapy pods in locations that do not require heat sinks or space for heat dissipation.

Domes 134 also aid in retaining TTP 100 at a particular location when TTP 100 is deployed within a retaining layer of clothing, i.e., TTP 100 is sandwiched between the retaining layer of fabric and a user's body and/or an inner fabric between the user's body and TTP 100. The non-planar outer surface 102 creates greater friction and increases the contact surface area between outer surface 102 and the retaining fabric. While the exemplary outer surface 102 in FIGS. 1-7 includes a plurality of domes 134, outer surface 102 may include any features configured to increase the contact surface area and create a non-planar outer surface 102. In addition, the number of features is not limited to four; rather there may be one or more non-planar features.

Figure 8A:
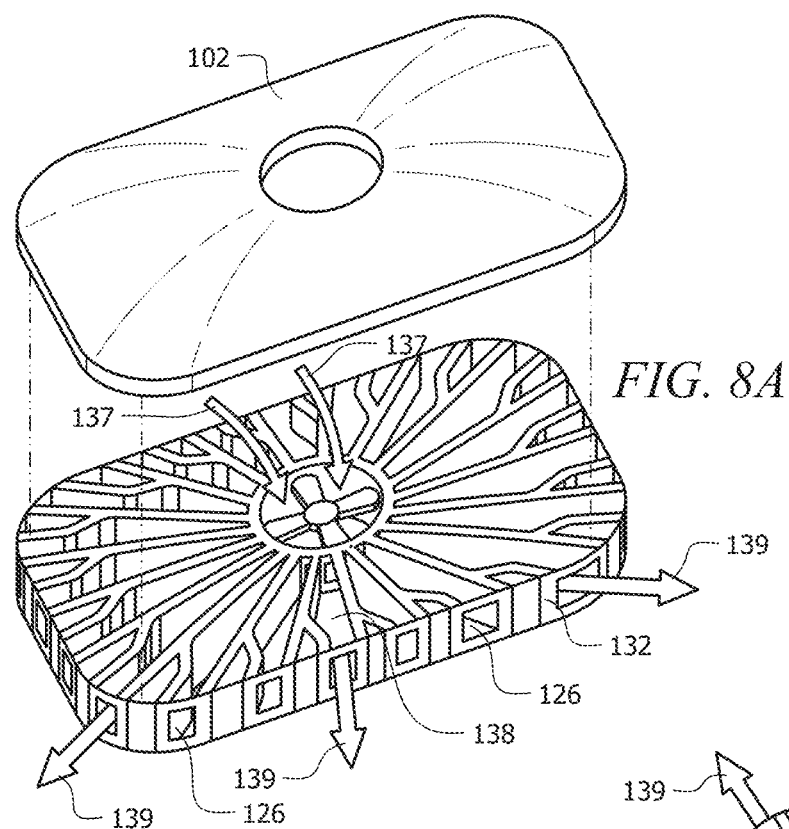
FIG. 8A is a perspective view of an embodiment of the present invention with the outer surface removed to show the internal cooling channels.
Figure 8B:
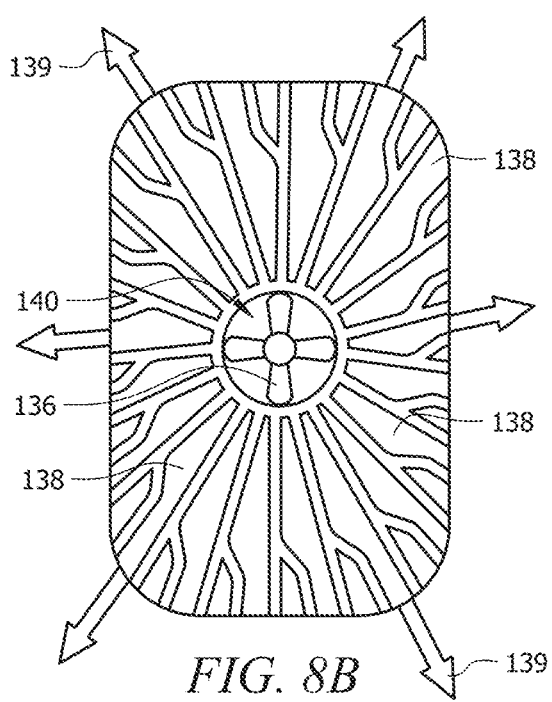
FIG. 8B is a top view of the embodiment depicted in FIG. 8A with the outer surface not depicted.
Figure 8C:
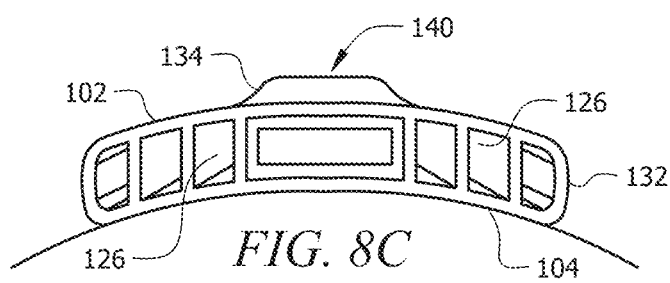
FIG. 8C is an end elevation view of the embodiment depicted in FIG. 8A.
Figure 9:
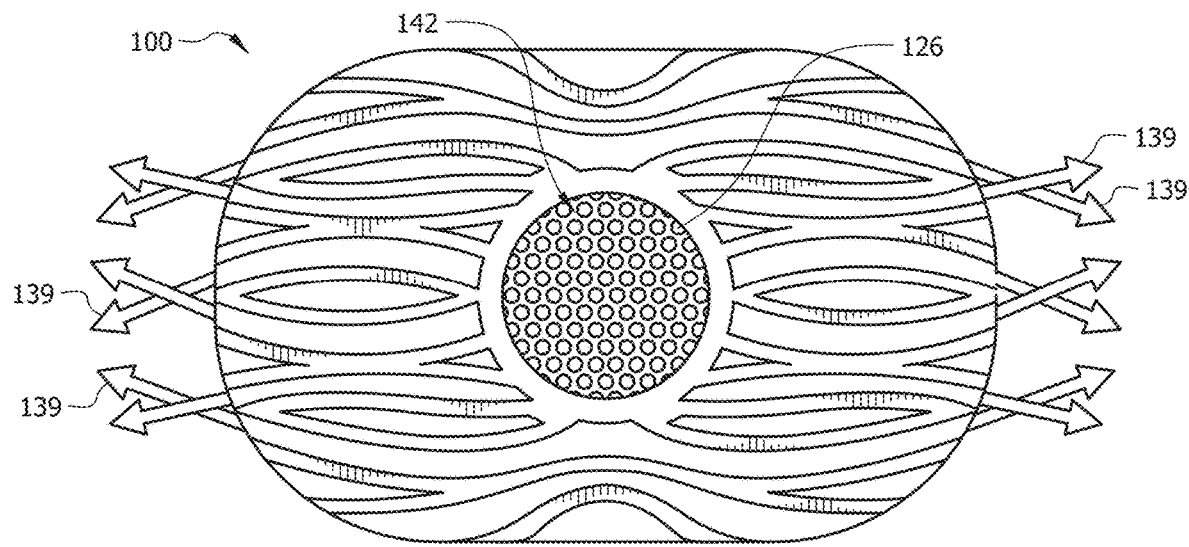
FIG. 9 is a top view of an embodiment of the present invention.

In some embodiments, as exemplified in FIG. 8C, dome structure(s) 134 house fan 136. Fan 136 is configured to direct hot air out of vent holes 126. Similar to the other electrical components, fan 136 is in electrical communication with batteries 106 through one or more wires 112 or other electricity transferring elements.

Some embodiments of main body 101 further include a plurality of cooling channels 138. Each cooling channel 138 is fluidically coupled to fan chamber 140 through proximal aperture 125. As such, air can pass between fan chamber 140 and cooling channels 138 through the proximal apertures 125. In some embodiments, as shown in FIGS. 8, fan 136 is configured to suck in air from adjacent outer surface 102 via vent holes 126 as exemplified by arrow 137 and force said air through cooling channels 138 and out of distal apertures 127 as exemplified by arrows 139. In some embodiments, fan 136 is configured to cause ambient air to flow in the opposite direction—in through distal apertures 127 disposed in side walls 132, through cooling channels 138, and out of fan chamber 140 through vent holes 126 above fan 136.

In some embodiments, cooling channels 138 are elongated channels with proximal apertures 125 (apertures closest to fan 136) and distal apertures 127 (apertures furthest from fan 136). Some embodiments of cooling channels 138 includes a series of baffles to redirect air flow. Some embodiments include channels that specifically direct air along the length of ETFEs 110 to aid in heat transfer from ETFEs 110 to the passing air. In some embodiments, cooling channels 138 run adjacent to at least 50% of the upper surface area of ETFEs 110 to aid in heat transfer from ETFEs 110 to the passing air. In some embodiments, cooling channels 138 run adjacent to at least 60% of the upper surface area of ETFEs 110 to aid in heat transfer from ETFEs 110 to the passing air. In some embodiments, cooling channels 138 run adjacent to at least 70% of the upper surface area of ETFEs 110 to aid in heat transfer from ETFEs 110 to the passing air. In some embodiments, cooling channels 138 run adjacent to at least 80% of the upper surface area of ETFEs 110 to aid in heat transfer from ETFEs 110 to the passing air. In some embodiments, cooling channels 138 run adjacent to at least 90% of the upper surface area of ETFEs 110 to aid in heat transfer from ETFEs 110 to the passing air.

Figure 13A:
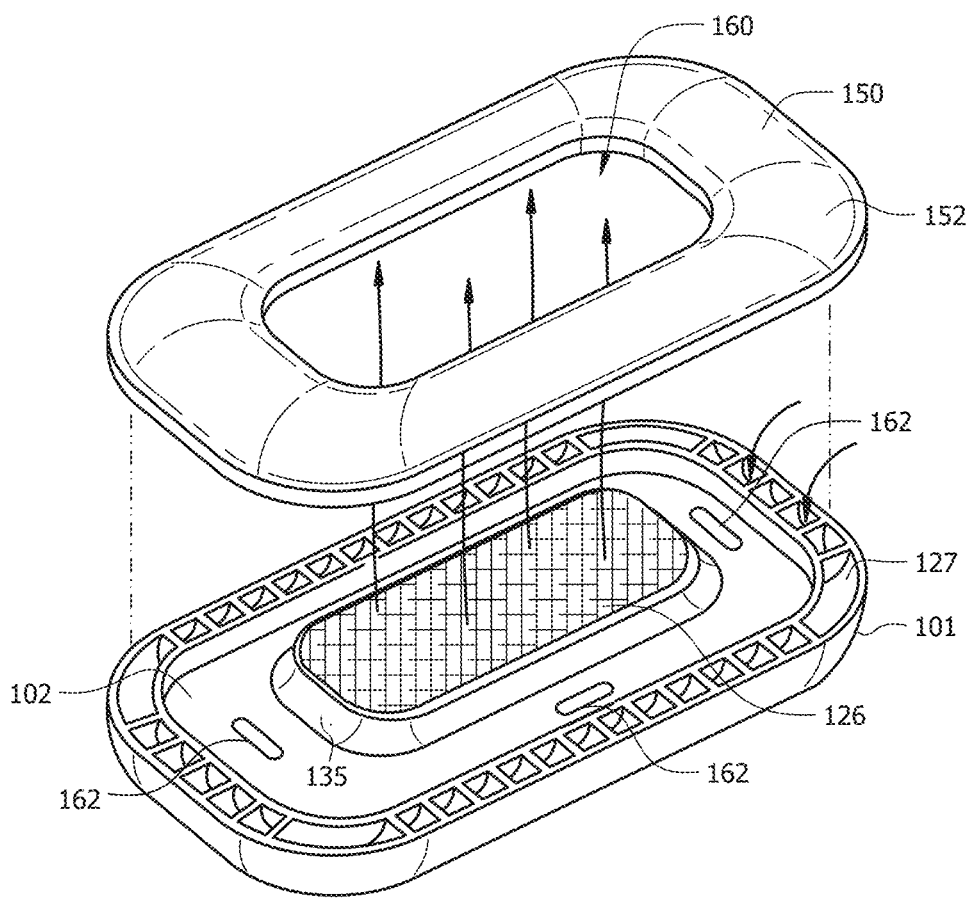
FIG. 13A is a perspective view of an embodiment of the present invention with the cover removed.
Figure 13B:
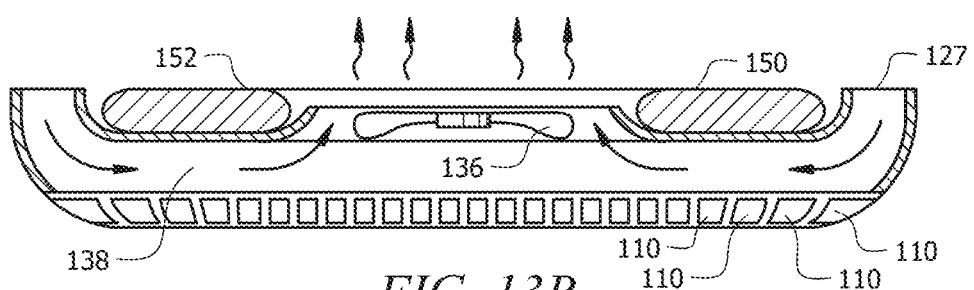
FIG. 13B is a side cross-sectional view of the embodiment depicted in FIG. 13A.
Figure 14:
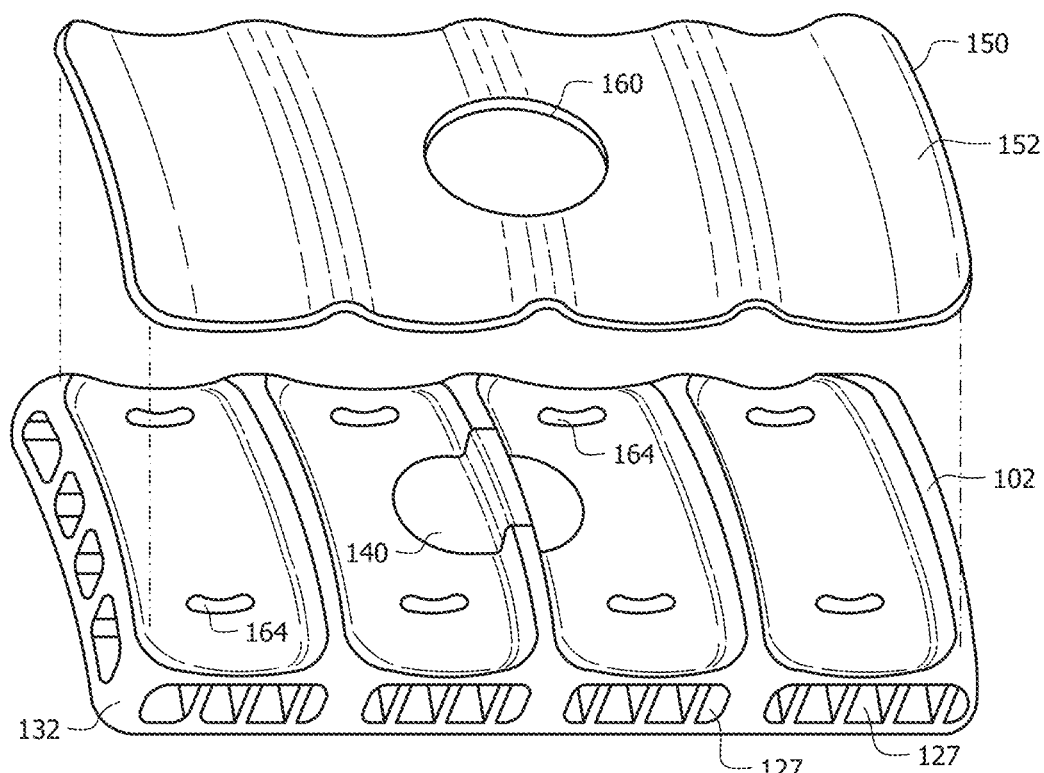
FIG. 14 is a perspective view of an embodiment of the present invention with the cover removed.

Some embodiments of cooling channels 138, such as those illustrated in FIGS. 8-9, 12, 14-18, and 20-22, include distal apertures 127 (could operate as inlets or outlets depending on the direction of the air flow) that direct air in a lateral direction as exemplified by arrows 139. These laterally discharging apertures 127 are typically disposed in sidewalls 132. However, some embodiments, such as those exemplified in FIGS. 13 and 19 include distal apertures 127 in outer surface 102.

Figure 10:
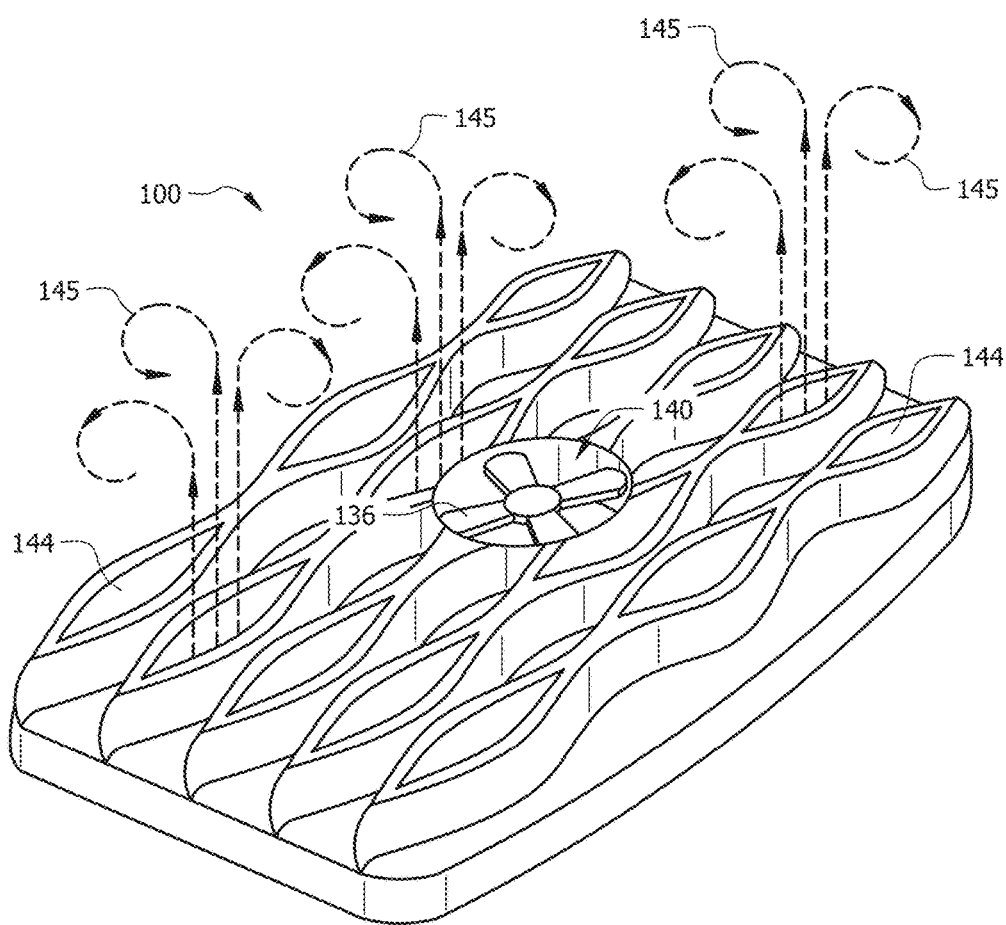
FIG. 10 is a top view of an embodiment of the present invention.

As depicted in FIG. 10, some embodiments include a plurality of chimneys 144. Chimneys 144 act as heat sinks/exchangers and/or can be in fluidic communication with fan 136 to dispel heat away from TTP 100 as exemplified by arrows 145.

Figure 11:
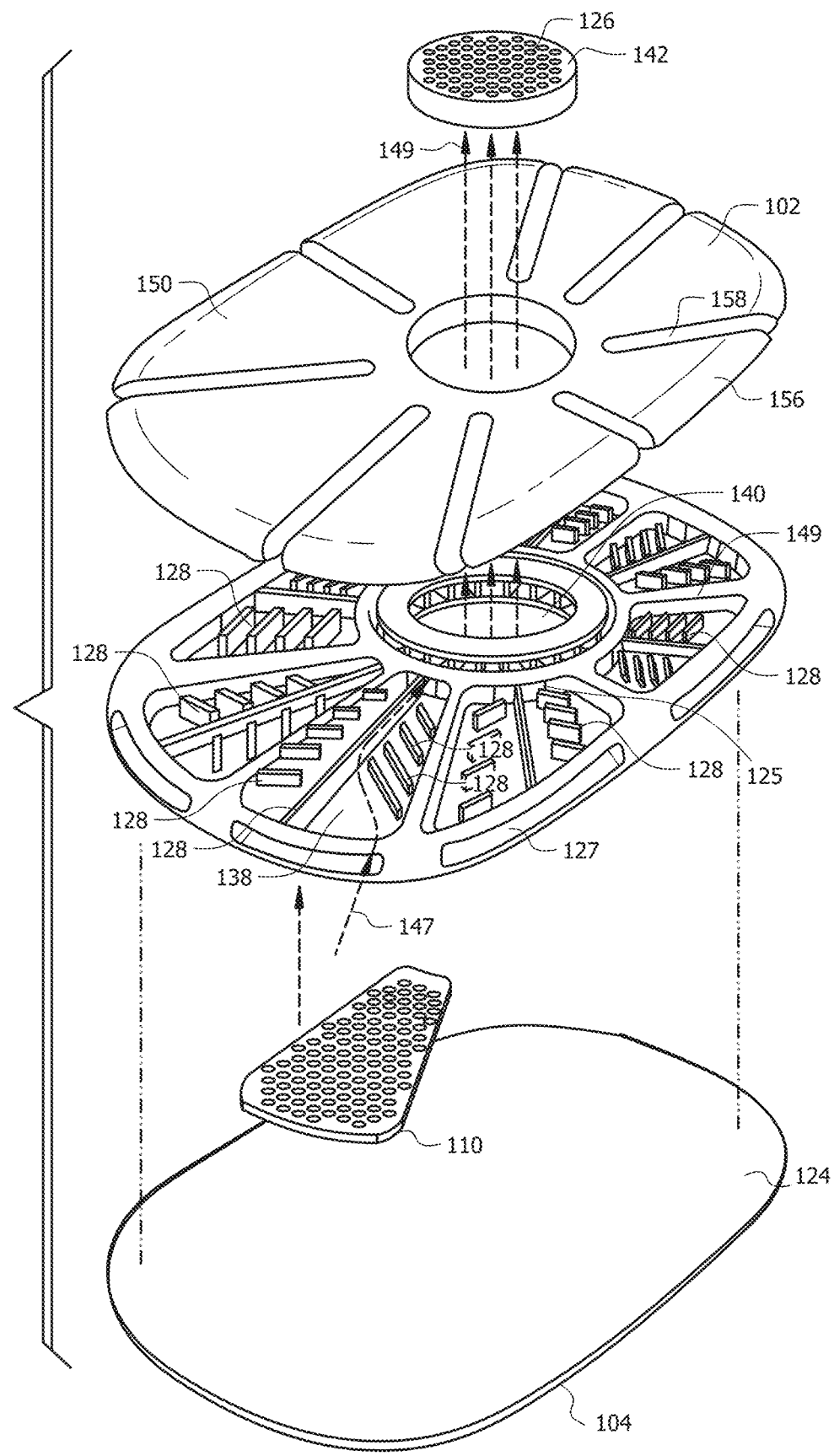
FIG. 11 is an exploded view of an embodiment of the present invention.
Figure 12A:
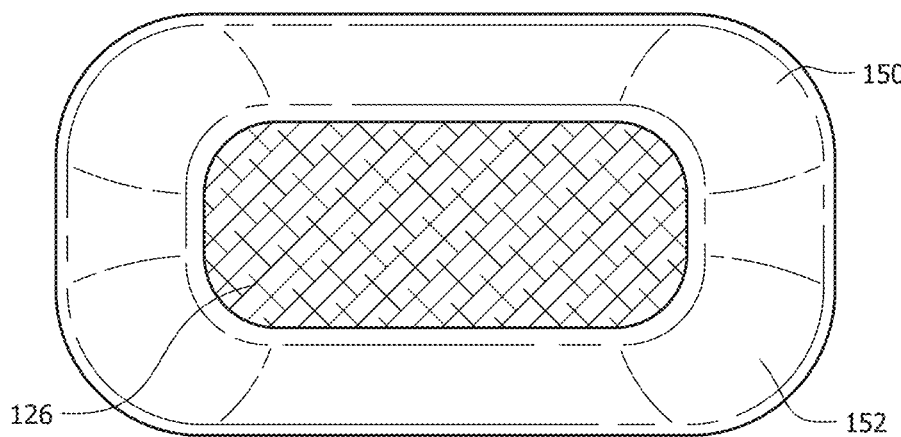
FIG. 12A is a top view of an embodiment of the present invention.
Figure 12B:
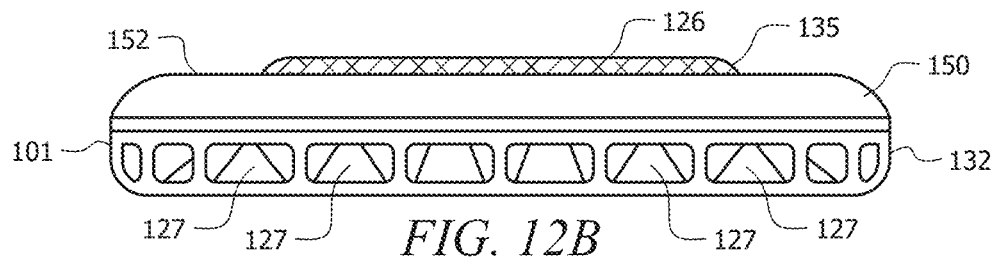
FIG. 12B is a side elevation view of the embodiment depicted in FIG. 12A.
Figure 12C:
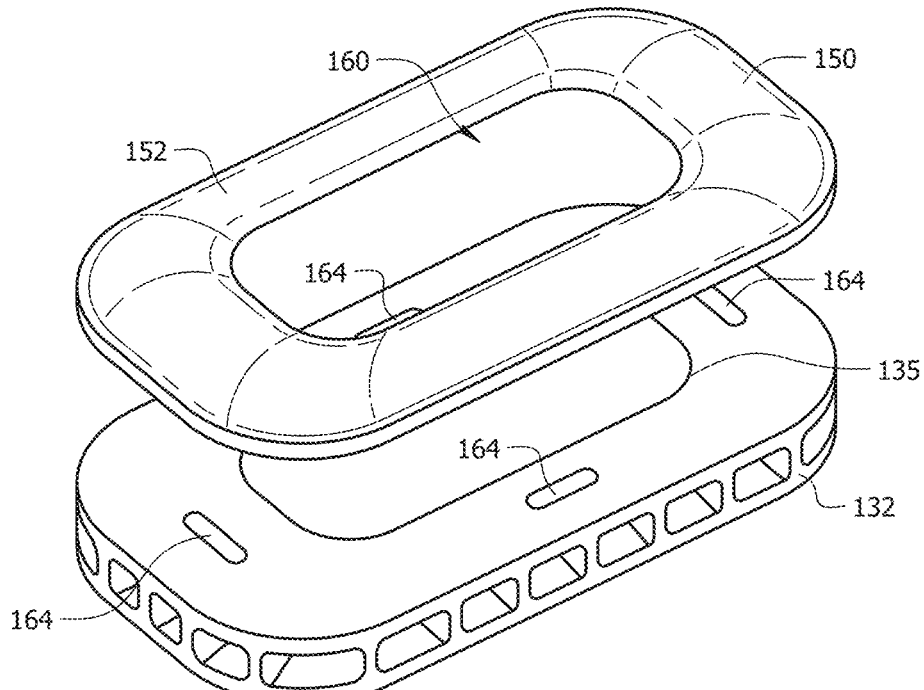
FIG. 12C is a perspective view of the embodiment depicted in FIG. 12A with the cover removed.

As depicted in FIG. 11, some embodiments include heat sinks/exchangers 128 within cooling channels 138. As ambient air is pulled through channels 138 and past heat sinks 128 (exemplified by arrow 147), the heat created from ETFEs 110 transfers to the passing air, which is vented through fan screen 142 (exemplified by arrow 149) from TTP 100 via fan 136 (not depicted in FIG. 11 to avoid clutter).

FIG. 11 also depicts an embodiment having a flexible chassis 149 comprised of flexible material such as TPU. ETFEs 110 reside below each cooling channel 138 (only one is depicted to avoid clutter), which are separated by flexible structural members that make up chassis 149. This arrangement helps allow TTP 100 to flex with the shape of the user's body. Some embodiments of chassis 149 and main body 101 include articulating joints or living/integral hinges at predetermined locations to allow TTP 100 to flex with the user's body.

In some embodiments, (see e.g., FIGS. 9 and 11) TTP 100 includes fan screen 142. Fan screen 142 acts as a barrier between fan 136 and external objects. In addition, fan screen 142 includes vent holes 126 to dissipate heat or inlet apertures 125 to allow ambient air to pass into fan chamber 140. In some embodiments, fan screen 142 is detachable from main body 101. In some embodiments, fan screen 142 is attachable to or integrated with a detachable cover.

As shown in FIGS. 11-21, some embodiments include removable cover 150 configured to interlock with main body 101. In some embodiments, removable cover 150 is configured to securely engage main body 101 to act as a clamp to trap a retaining fabric. For example, the garment disclosed in Applicant's U.S. Pat. No. 8,876,875 includes a large open receiving compartment between an inner layer of fabric and a retaining layer of fabric. Cover 50 of the present invention can be used in conjunction with main body 101 to clamp onto a retaining object, such as the retaining fabric in U.S. Pat. No. 8,876,875 or a tight fitting clothing item.

Figure 15:
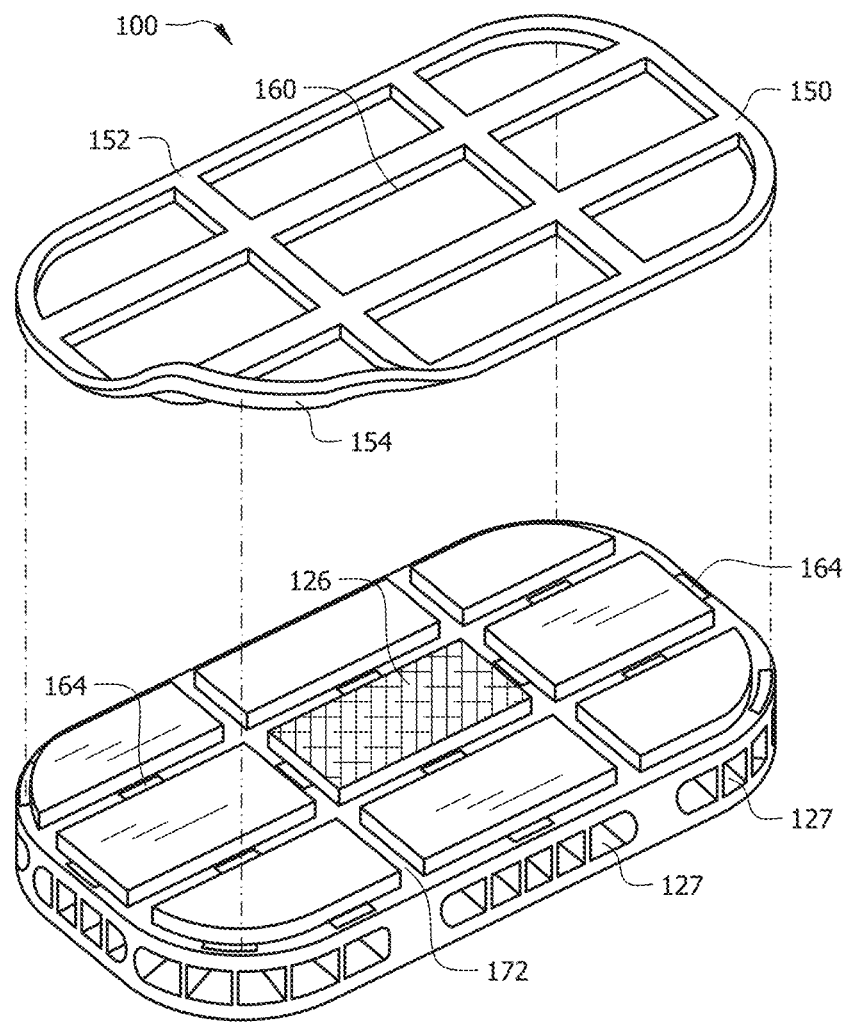
FIG. 15 is a perspective view of an embodiment of the present invention with the cover removed.
Figure 19:
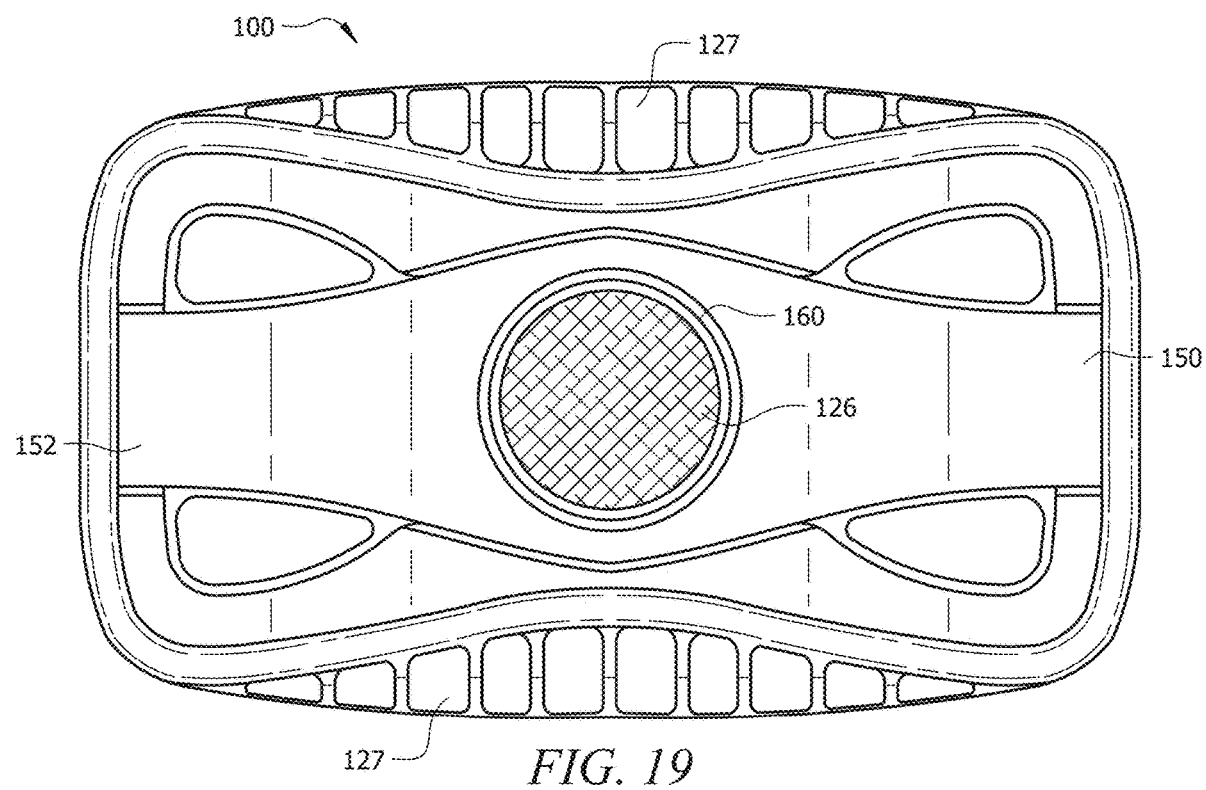
FIG. 19 is a top view of an embodiment of the present invention.

In some embodiments, cover 150 is comprised of a flexible material allowing it to conform to the variable shape/curvature of main body 101, as exemplified in FIGS. 15 and 19. For example, cover 150 may be comprised of molded polycarbonate.

Figure 21A:
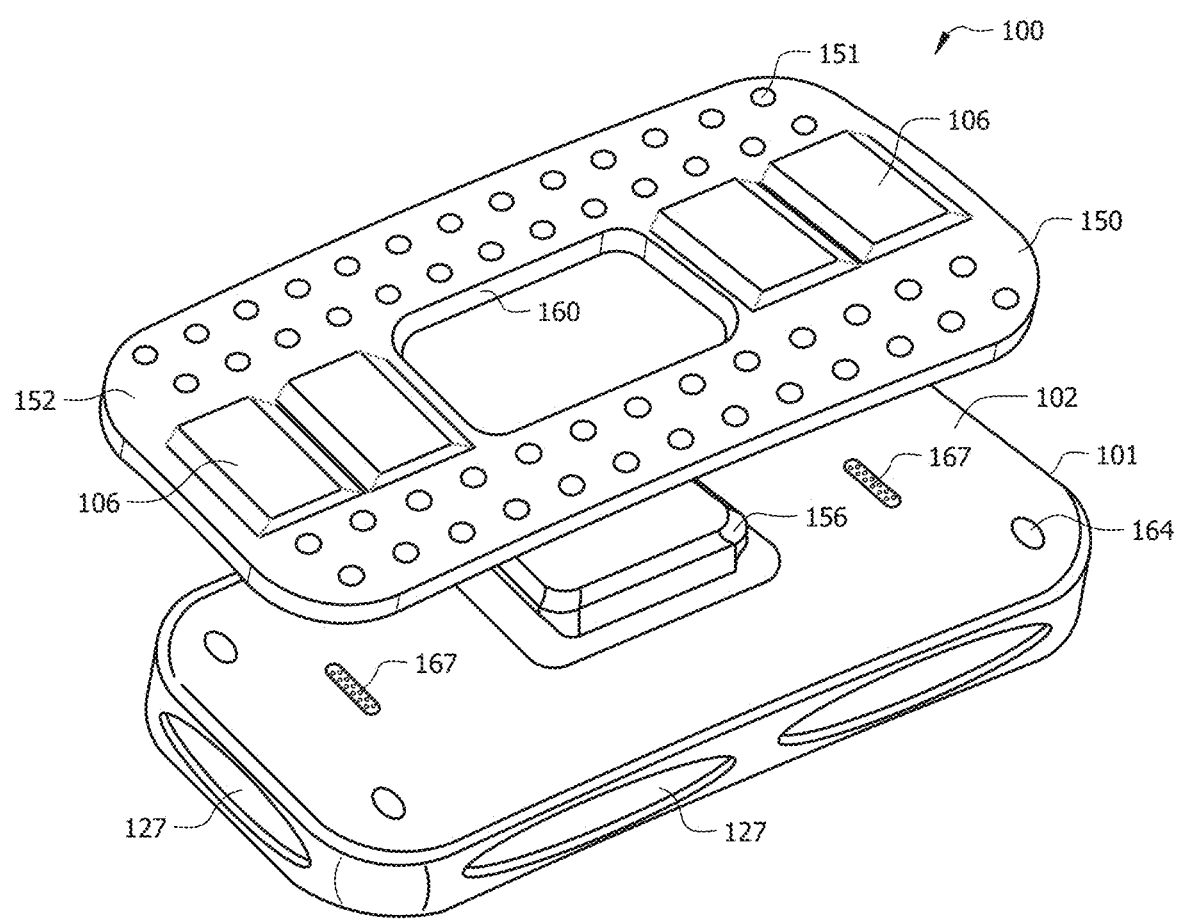
FIG. 21A is a perspective view of an embodiment of the present invention with the cover removed.
Figure 21B:
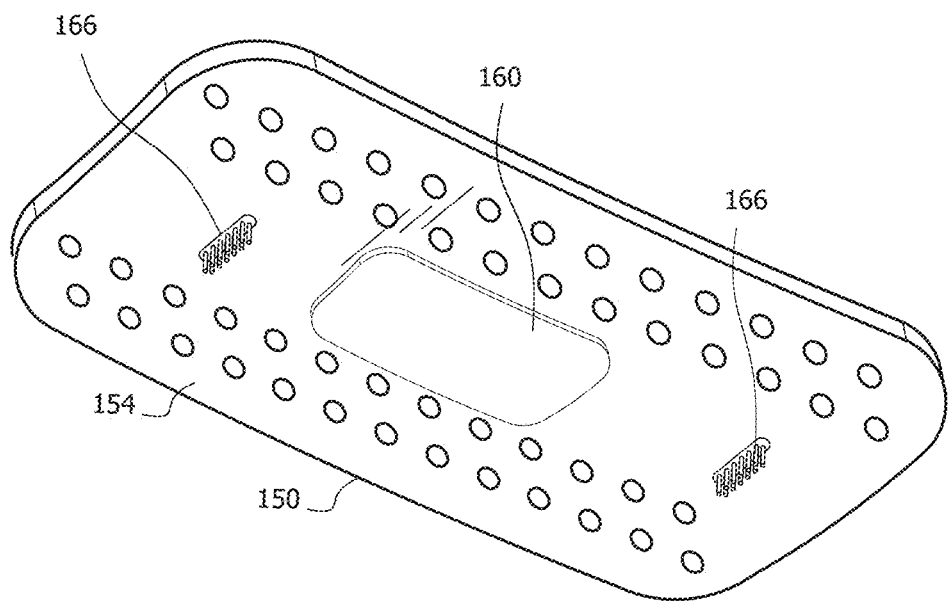
FIG. 21B is a bottom perspective view of an embodiment of the cover from the embodiment in FIG. 21A.
Figure 21C:
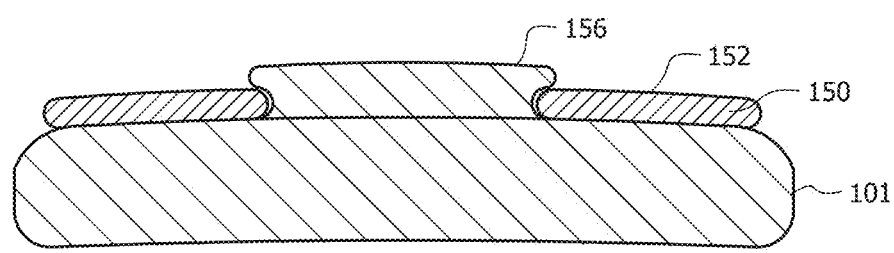
FIG. 21C is an end elevation view of the embodiment depicted in FIG. 21A.

Some embodiments of cover 150 are comprised of a material with minimal thermal conductivity to ensure that cover 150 does not absorb or retain heat intended to be dissipated from TTP 100. For the same reason, some embodiments have a minimal thickness (see e.g., FIGS. 14-18) and/or minimal surface area (see e.g., FIGS. 15-18). Some embodiments, as depicted in FIG. 21, include perforations 151 extending through cover 150 to further aid in dissipation of heat. In addition to or alternatively, some embodiments of cover 150 include dimples, projections, or other surface indentations or projections that increase the surface area of outer surface 152 of cover 150. Some embodiments include cover 150 having vacuum chambers to prevent the transfer of heat through cover 150.

As previously explained, cover 150 is configured to interconnect with main body 101. Some embodiments include mechanical interlocking features, including but not limited to hook and loop fasteners, threaded connections, cam connections, rotational connectors, frictional receipts, etc. For example, as exemplified in FIG. 11, cover 150 may include outer retaining walls 156 having an arcuate cross-section configured to snap around curved side walls 132. In other words, retaining walls 156 are a clip-like compliant mechanical lip that can flex around a portion of main body 101. Such embodiments may also include slots 158 extending in a generally lateral direction about cover 150. Slots 158 allows subsections of cover 150 to independently flex thereby allowing cover 150 to flex when cover 150 is being forced onto main body 101 such that retaining walls 156 at least partially encircle side walls 132.

In some embodiments, as depicted in FIGS. 21, main body 101 includes the mechanical interlocking feature, such as arcuate retaining wall 156. Regardless of whether main body 101 or cover 150 includes the mechanical interlocking features, both components are operably shaped to interconnect in a mechanical fashion.

In some embodiments, the fit of cover 150 around main body 101 is sufficiently sized to accommodate a retaining fabric when cover 150 is attached to main body 101. If the fit between cover 150 and main body 101 is too tight, the retaining fabric cannot be trapped between the two. In other words, some embodiments, sufficiently large enough that the lack of a retaining fabric between the two results in a loose fit in which cover 150 can slide about main body 101 instead of being retained in a set position. In some embodiments, the fit between cover 150 and main body 101 is sufficient to accommodate a mesh fabric having a thickness between 0.006 and 0.04 inches. In some embodiments, the fit between cover 150 and main body 101 is sufficient to accommodate a mesh fabric having a thickness between 0.0197 and 0.0394 inches.

Some embodiments of TTP 100 include one or more magnets 162 disposed in cover 150 or adjacent to inner surface 154 of cover 150. Main body 101 also includes one or more magnets 164 disposed therein or adjacent to outer surface 102. In some embodiments, one or more magnets is provided in cover 150 or main body 101, wherein the magnets are configured to magnetically engage magnets or metallic components within the main body 101 or cover 150.

Figure 16A:
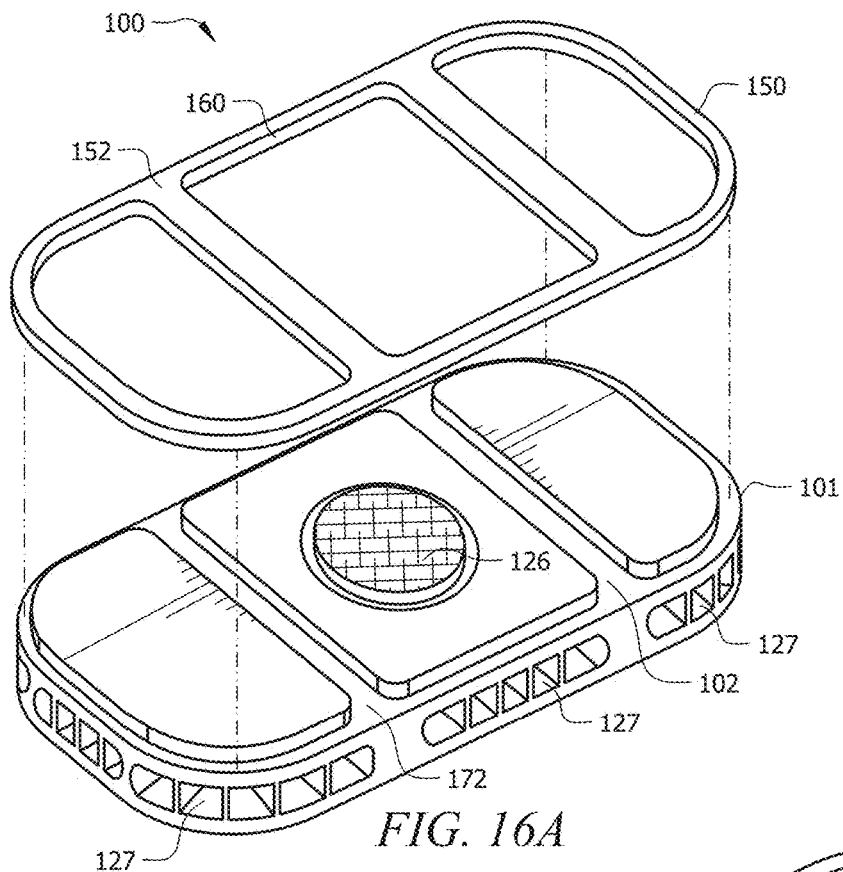
FIG. 16A is a perspective view of an embodiment of the present invention with the cover removed.
Figure 16B:
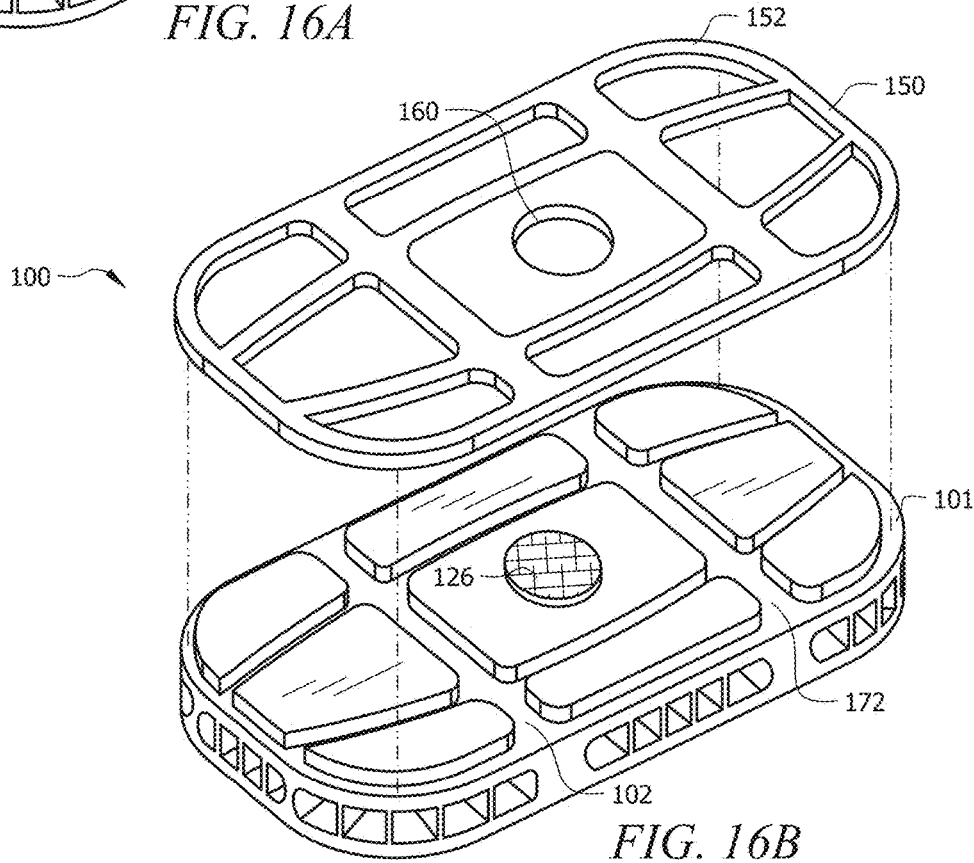
FIG. 16B is a perspective view of an embodiment of the present invention with the cover removed.

Some embodiments, as exemplified in FIGS. 16, include main body 101 having a plurality of female recesses sized to receive cover 150 in a press fit or friction fit manner when a retaining fabric resides between cover 150 and main body 101. Some embodiments may rely on charging pins 166 and pin receipts 167 (see e.g., FIG. 21) to aid in or provide the fastening between cover 150 and main body 101. The use of charging pins 166 is most useful when the retaining fabric is a mech fabric thereby allowing charging pins 166 to pass through the retaining fabric without damaging the fabric.

Cover 150 is also shaped to match the contours of main body 101 and ensure that vent holes 126 and distal apertures 127 remain unobstructed (see e.g., FIG. 19). As such, some embodiments include aperture 160 configured to align with fan screen 142 or the array of vent holes 126. Some embodiments also include unique shapes having at least one line of asymmetry to ensure that cover 150 can only interconnect with main body 101 in the proper orientation.

In some embodiments, main body 101 includes raised portion 135 which at least partially make up fan chamber 140. Raised portion 135 may be necessary to accommodate fan 136. However, the remaining portion(s) of outer surface 102 of main body 101 have a smaller thickness. In such embodiments, aperture 160 in cover 150 is configured to receive raised portion 135 of main body 101. In some embodiments, as exemplified in FIGS. 12-13, cover 150 has a thickness equal to or less than the distance that raised portion 135 extends from outer surface 102 of main body 101. This receipt also helps ensure proper alignment of cover 150 with main body 101.

Figure 17:
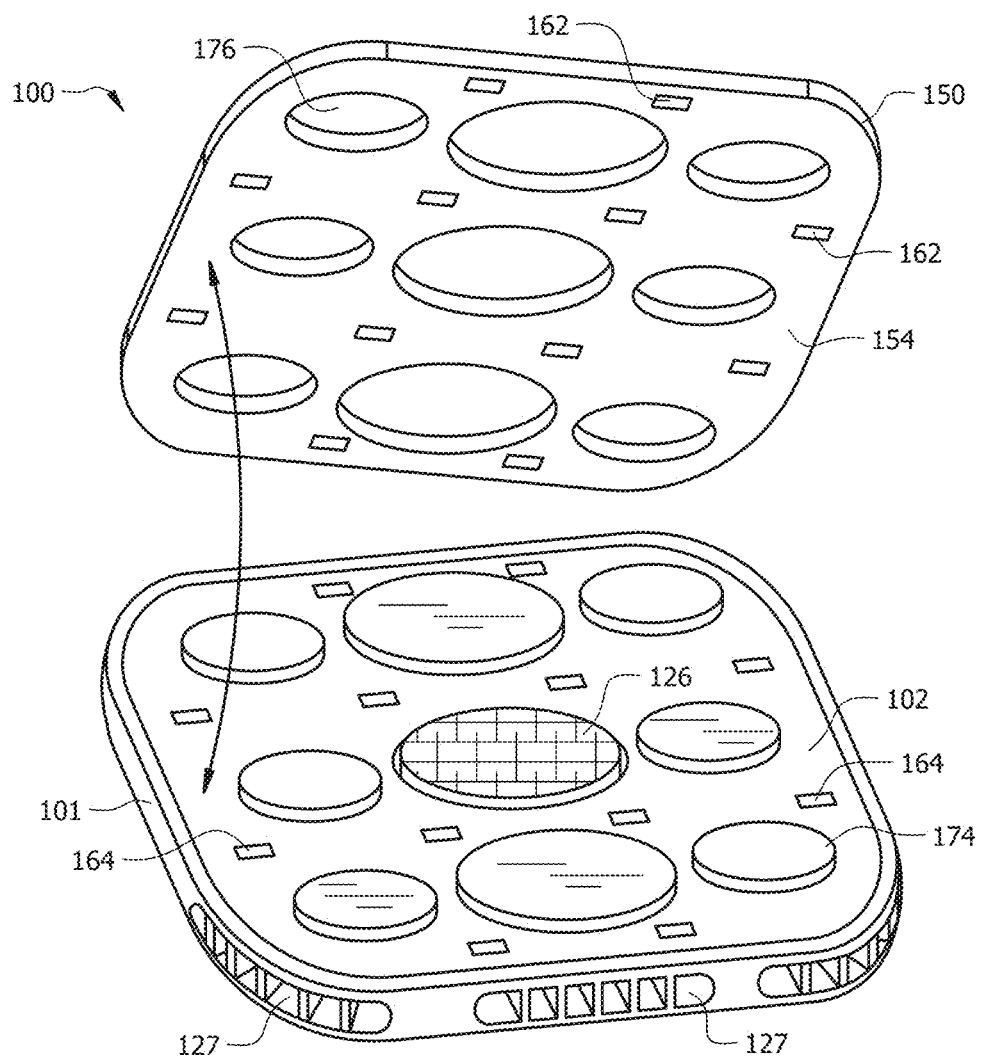
FIG. 17 is a perspective view of an embodiment of the present invention with the cover removed.
Figure 18:
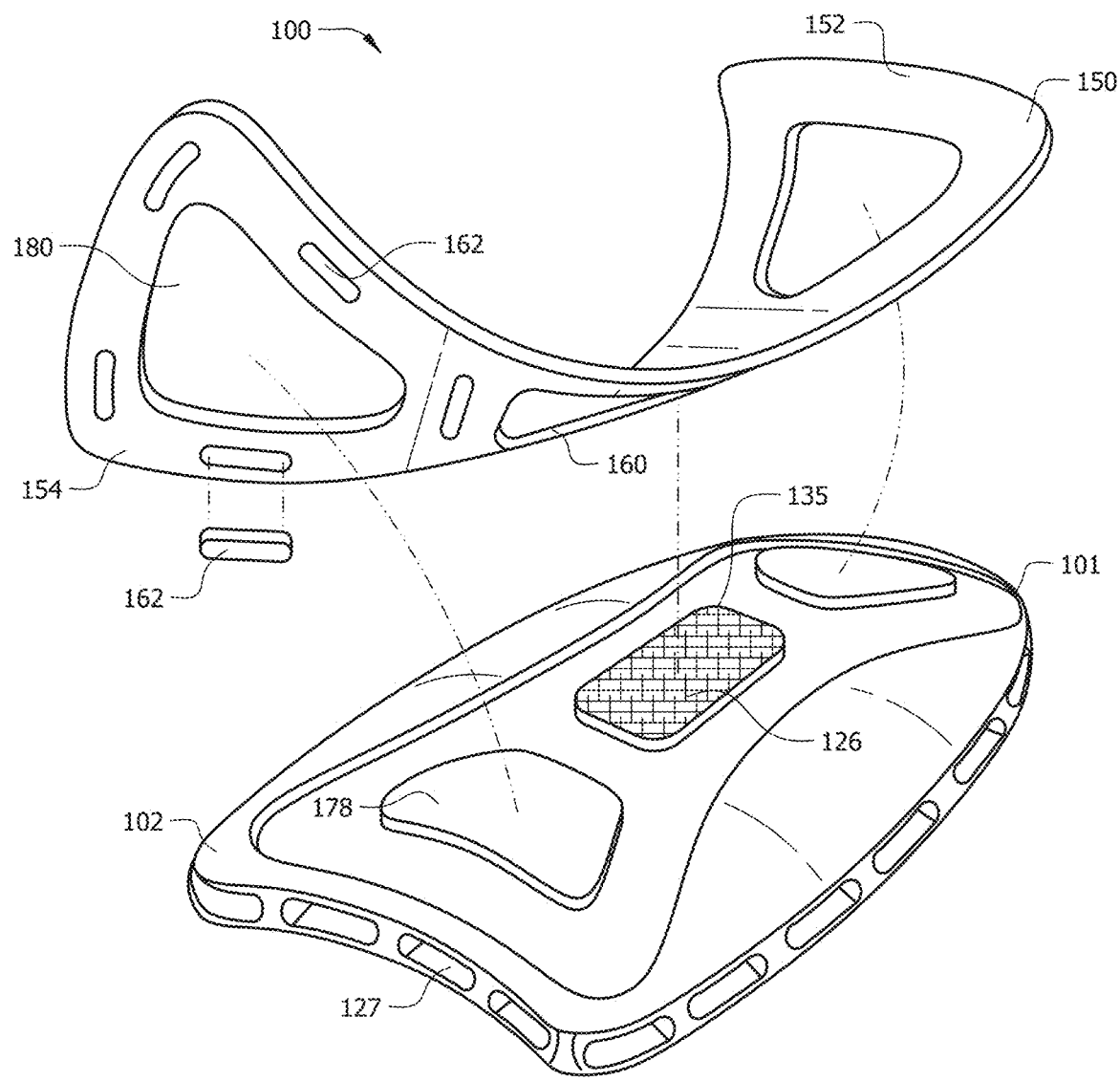
FIG. 18 is a perspective view of an embodiment of the present invention with the cover removed.

Moreover, some embodiments have male keys on main body 101 and corresponding female key receipts on cover 150, or vice versa. For example, FIG. 14 includes ridges 168 on main body 101 and ridge receipts 170 on cover 150; FIGS. 15-16 include a grid-like cover 150 with receipts 172 on main body 101; FIG. 17 includes cylindrical projections 174 on main body 101 and circular receipts 176 in cover 150; and FIG. 18 includes polygonal projections 178 on main body 101 and polygonal receipts 180 in cover 150.

In some embodiments, the features on cover 150 and/or main body 101 are specifically designed so that cover 150 can only attach to main body 101 in one or more predetermined orientations. This aspect is of particular importance when cover 150 houses the one or more batteries 106 (see e.g., FIGS. 20-21) for powering or charging main body 101 and is required to be in a specific orientation to provide main body 101 with electrical power. For example, charging pins 166 on cover 150 must be aligned with pin receipts 167 (see FIG. 21). As another example, some embodiments my include cover 150 having wireless charging transmitters 190 and main body having wireless charging receivers 192, which must be within a certain distance from each other to transfer power from cover 150 to main body 101.

Figure 20A:
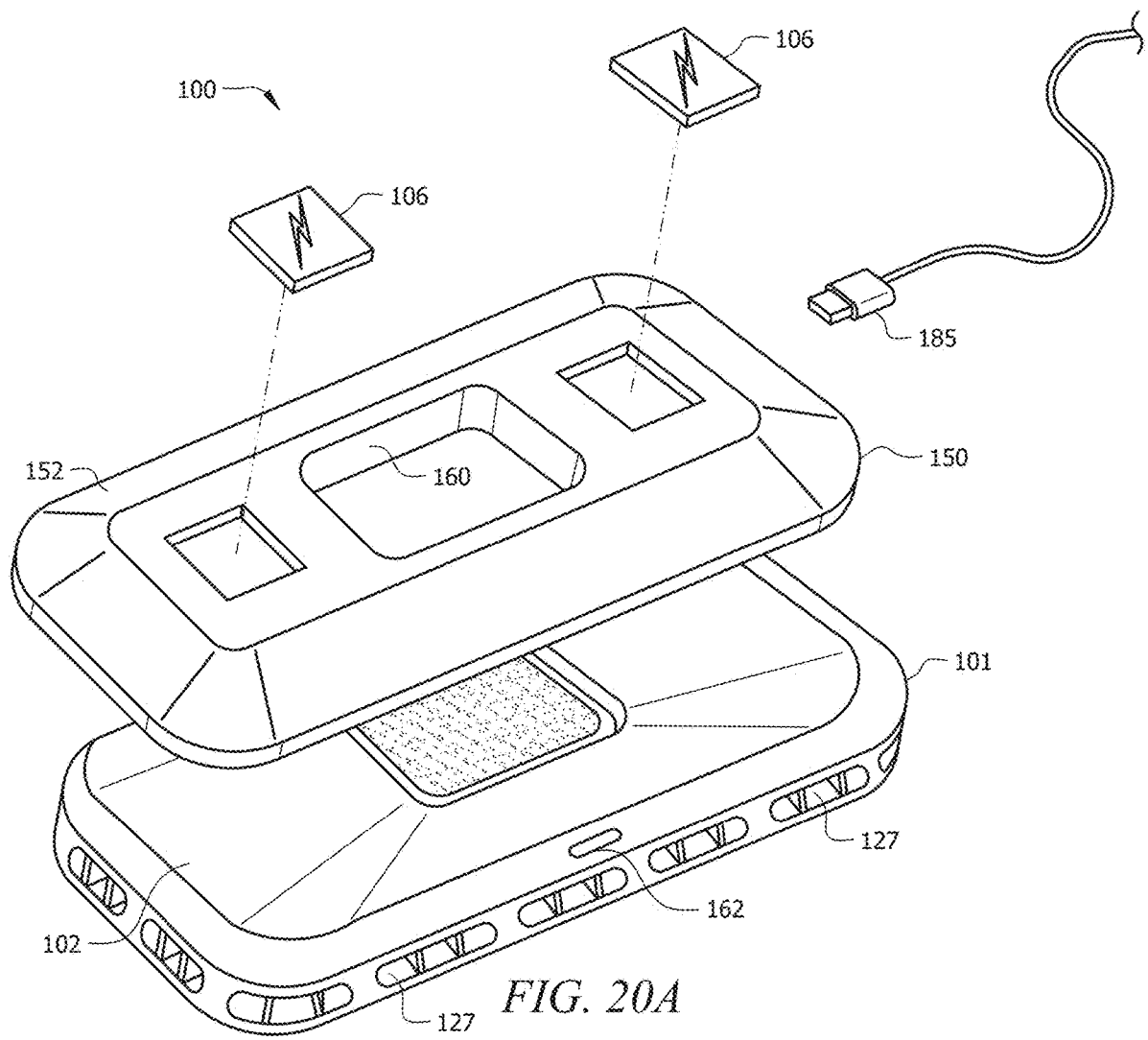
FIG. 20A is a perspective view of an embodiment of the present invention with the cover removed.
Figure 20B:
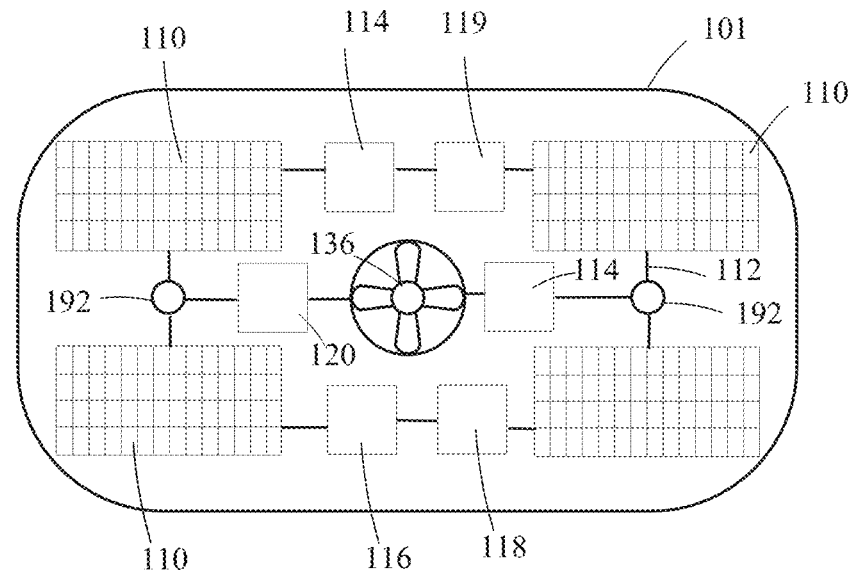
FIG. 20B is a top plan view of the internal components of an embodiment of the main body from FIG. 20A.
Figure 20C:
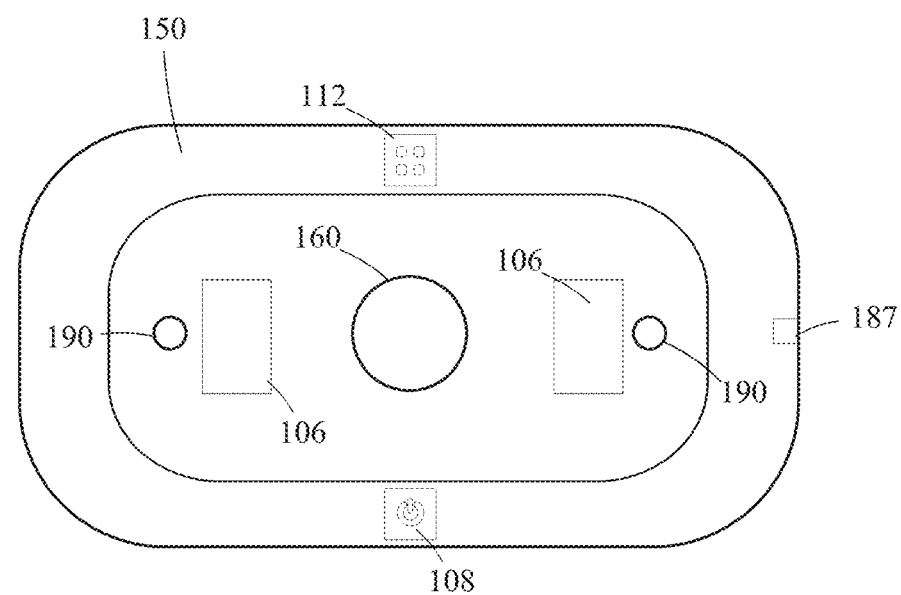
FIG. 20C is a top plan view of the internal components of an embodiment of the cover from FIG. 20A.

As previously mentioned, one or more of the various components of TTP 100 may be housed within cover 150 rather than main body 101 (see e.g., FIGS. 20-21). Some embodiments specifically house batteries 106 within cover 150 thereby allowing a user to simply switch out one cover for another to increase the operational time of TTP 100 without having to remove TTP 100 from its position adjacent to a certain part of a user's body. These embodiments are configured to transfer power from covers 150 to main body 101 to power at least the ETFEs 110 housed in main body 101. Some embodiments used charging pins 166 (e.g., pogo pins) and pin receipts 167. Some embodiments may include wireless power transfer between cover 150 and main body 101 to allow a non-mesh retaining fabric to reside between cover 150 and main body 101. In some embodiments, cover 150 includes an accessible battery housing having a cover that can be opened to replace the batteries as needed. Some embodiments include a charging port 187 disposed in each cover 150 to charge covers 150 when not in use or alternatively provide power when the user is stationary and near a power outlet.

Some embodiments of the present invention include TTP 100 and a retaining garment. The retaining garment may be a single layer compression clothing garment or may be a multi-layer garment like the garment disclosed in U.S. Pat. No. 8,876,875 having a retaining garment layer. The retaining garment resides between cover 150 and main body 101. Alternatively, the outer surface of cover 150 or main body 101 can include one or more bulbous shapes (or any non-planar shapes or non-homogenous cross-sectional shapes) projecting outwards away from the inner surface 104 of main body 101, and the retaining garment applies a tension onto TTP 100 to retain TTP 100 at a particular location with respect to a user's body. Due to the interconnection of TTP 100 and the retaining garment, TTP 100 can be positioned anywhere on the user's body in which a retaining garment is positioned.

In some embodiments, the retaining garment or retaining garment layer is mesh to allow for better venting of heat and ease for interconnection of TTP 100 with the retaining garment or retaining garment layer. In such embodiments, TTP 100 can include charging pins 166 sized to pass through the mesh holes. Alternatively, the outer surface of TTP 100 may include projections configured to pass through the mesh holes. In some embodiments, said projections do not cover the vent holes 126 or distal apertures 127.

Some embodiments of TTP 100 may include silicon gripping elements disposed on the outer surface of TTP 100 to aid in retaining the therapy pod against a user's body via a compressive garment. The gripping elements may be comprised of any material that increases the static friction of the therapy pod. Furthermore, the entire outer surface may be comprised of material that increases the static friction of the therapy pod. Some embodiments include gripping elements not disposed overtop of the vent holes 126 to allow for adequate dissipation of heat from ETFEs 110.

Figure 22:
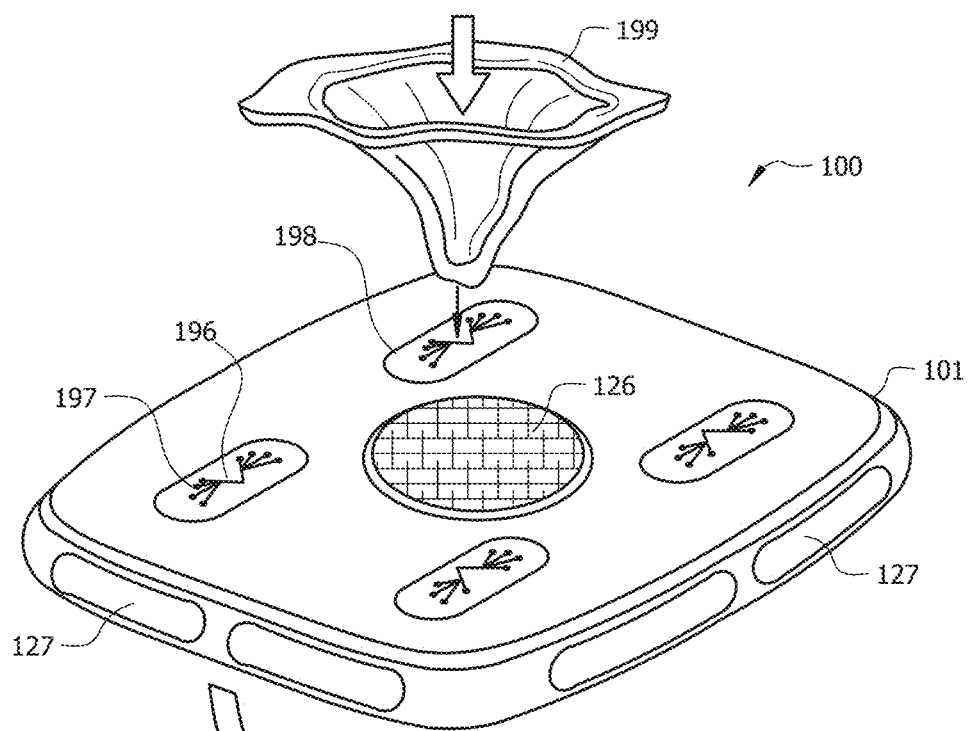
FIG. 22 is a perspective view of an embodiment of the present invention and an illustration of the embodiment in use.
Figure 22:
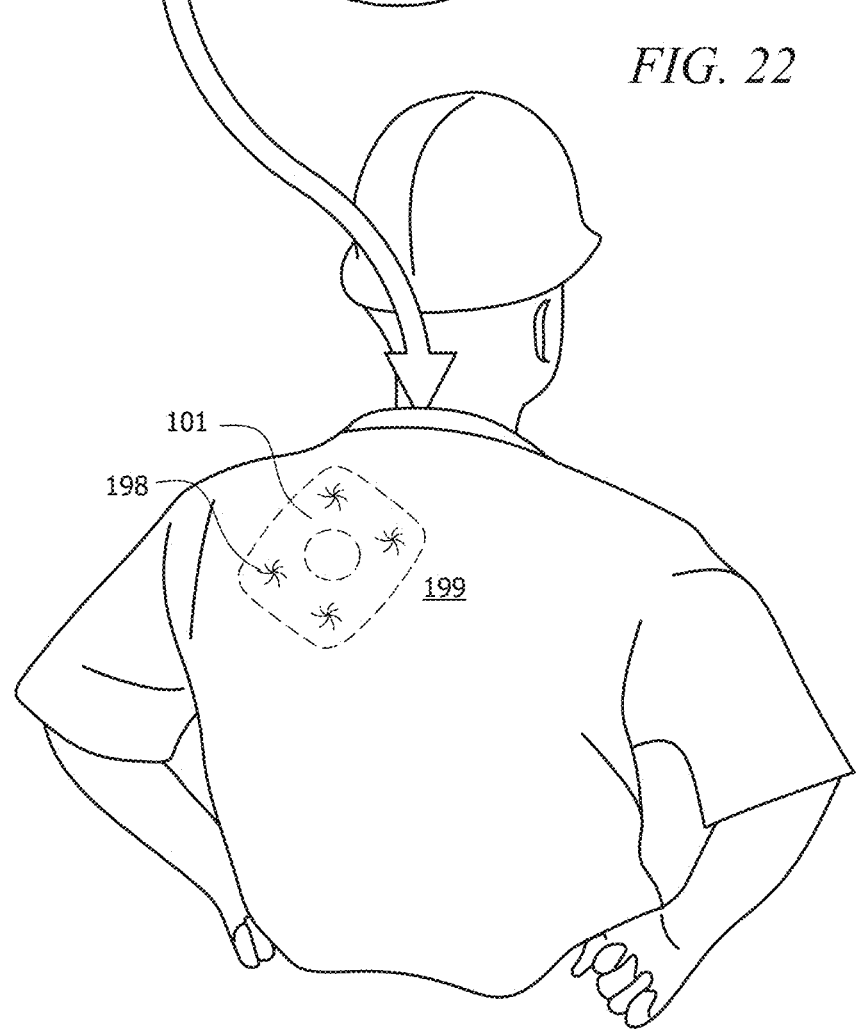

Referring now to FIG. 22, some embodiments of TTP 100 include starburst connector 198 having a plurality of slits 197 and compliant flaps 196 covering a fabric retention receipt. The starburst connector is similar to a cross-slit valve in operation but may include more than four compliant flaps. Starburst connector 198 is configured to receive a portion of retaining garment 199 and compliant flaps 196 retain the inserted portion of retaining garment 199.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all the generic and specific features of the invention herein described, and all statements of the scope of the invention that, as a matter of language, might be said to fall therebetween.

What is claimed is:

1. A thermal therapy pod, comprising:
   an elongated thin main body having a thickness residing between an inner surface and an outer surface;
   an electric powered thermal transferring element residing between the inner surface and the outer surface;
   a fan configured to dissipate heat, created from operating the electric powered thermal transferring element, to an ambient environment;
   a vent in the outer surface of the main body, wherein the heat dissipated by the fan exits the main body through the vent in a direction opposite the inner surface of the main body;
   a removable cover configured to temporarily interconnect with the main body, wherein the cover includes:
      an aperture configured to align with the vent in the main body when the cover is interconnected with the main body;
      a battery;
      a power transferring element configured to transfer electrical power from the battery to the main body for operating the electric powered thermal transferring element and the fan;
   one or more recesses in the outer surface of the main body, the one or more recesses further including:
      a size and shape configured to receive at least a portion of a body section of the removable cover;
      a depth extending towards the inner surface of the main body;
   the cover having a thickness equal to or less than the depth of the one or more recesses, such that the cover does not extend outwardly beyond the outer surface of the main body;
   whereby receipt of the received portion of the body section of the cover within the one or more recesses increases an amount of surface area of a clothing item in contact with the main body and the cover when the clothing item is retained between the main body and the cover.

2. The thermal therapy pod of claim 1, further including:
   the power transferring element including one or more charging pins on the cover; and
   one or more charging pin receipts on the main body, wherein each charging pin receipt is positioned to receive a corresponding charging pin when the cover is interconnected with the main body;
   wherein the charging pin receipts are sized to pass through holes in a mesh fabric on a user's clothing item.

3. The thermal therapy pod of claim 1, further including:
   the power transferring element including a wireless power transmitter disposed in the cover;
   a wireless power receiver disposed in the main body; and
   the wireless power transmitter and wireless power receiver positioned at predetermined positions, such that the power transmitter is configured to transfer power to the wireless power receiver when the cover is interconnected with the main body.

4. The thermal therapy pod of claim 1, further including a charging port or wireless power receiver disposed in the cover for recharging the battery.

5. The thermal therapy pod of claim 1, further including:
   a current switching circuit, wherein the current switching circuit is configured to control a direction of a current to the electric powered thermal transferring element; and
   the electric powered thermal transferring element having an application side facing towards the inner surface of the main body of the thermal therapy pod and a dissipation side facing towards the outer surface of the main body of the thermal therapy pod;
   wherein the application side produces heat when the current flows in a first direction and becomes cold when the current flows in a second, opposite direction.

6. The thermal therapy pod of claim 1, further including a wireless communication system configured to communicate with a mobile device.

7. The thermal therapy pod of claim 1, further including a plurality of vent holes through which the fan can discharge heat, wherein the plurality of vent holes are configured to direct heat away from the inner surface of the main body.

8. The thermal therapy pod of claim 1, further including:
   a plurality of cooling channels, each cooling channel including:
      being in fluidic communication with the fan;
      a proximal aperture leading to the fan;
      a distal aperture leading out of the main body;
   whereby the fan directs air through the cooling channels to discharge heat from the electric powered thermal transferring element.

9. The thermal therapy pod of claim 8, wherein each cooling channel passes along the electric powered thermal transferring element.

10. The thermal therapy pod of claim 8, wherein the distal apertures are oriented to draw in or discharge air away from the inner surface of the main body.

11. The thermal therapy pod of claim 1, further including a heat sink residing in overlying relation to the electric powered thermal transferring element.

12. The thermal therapy pod of claim 1, further including a plurality of magnets disposed within the cover or the main body, wherein the magnets are configured to interconnect the cover to the main body.

13. The thermal therapy pod of claim 1, wherein the cover and the main body are flexible and resilient, thereby ensuring that the thermal therapy pod can flex about contours of a user's body.

14. The thermal therapy pod of claim 1, further including a thermally conductive layer between an application surface of the electric powered thermal transferring element and the inner surface of the main body, wherein the thermally conductive layer is comprised of thermally conductive material.

15. The thermal therapy pod of claim 1, further including a thermostat for determining a temperature of the thermal therapy pod.

16. The thermal therapy pod of claim 1, further including male and corresponding female components for aligning and interconnecting the cover with the main body.

17. The thermal therapy pod of claim 1, wherein the interconnection of the cover and the main body is sized to accommodate a retaining fabric between the cover and the main body when the cover and main body are interconnected.

18. A thermal therapy pod, comprising:
- an elongated thin main body having a thickness residing between an inner surface and an outer surface;
- an electric powered thermal transferring element residing between the inner surface and the outer surface;
- a fan configured to dissipate heat, created from operating the electric powered thermal transferring element, to an ambient environment;
- a vent in the outer surface of the main body, wherein the heat dissipated by the fan exits the main body through the vent in a direction opposite the inner surface of the main body;
- a current switching circuit, wherein the current switching circuit is configured to control a direction of a current to the electric powered thermal transferring element;
- the electric powered thermal transferring element having an application side facing towards the inner surface of the main body of the therapy pod and a dissipation side facing towards the outer surface of the main body of the therapy pod;
- wherein the application side produces heat when the current flows in a first direction and becomes cold when the current flows in a second, opposite direction;
- a battery configured to power the fan and electric powered thermal transferring element;
- a removable cover configured to temporarily interconnect with the main body, the cover including an aperture configured to align with the vent in the main body when the cover is interconnected with the main body;
- one or more recesses in the outer surface of the main body, the one or more recesses further including:
  - a size and shape configured to receive at least a portion of a body section of the removable cover;
  - a depth extending towards the inner surface of the main body, thereby allowing the received portion of the cover to reside below the outer surface of the main body;
  - whereby receipt of the portion of the removable cover configured to fit within the one or more recesses increases an amount of surface area of a clothing item in contact with the main body and the cover when the clothing item is retained between the main body and the cover;
  - one or more magnets, each of the one or more magnets disposed within a corresponding recess of the one or more recesses, and the one or more magnets are configured to magnetically engage the cover;
- wherein the magnetic engagement of the cover and the main body is configured to accommodate a clothing item between the cover and the main body.

19. The thermal therapy pod of claim 18, wherein the cover houses the battery and includes a power transferring element configured to transfer electrical power from the battery to the main body for operating the electric powered thermal transferring element and the fan.

* * * * *